US009550036B2

(12) United States Patent
Hoekman et al.

(10) Patent No.: US 9,550,036 B2
(45) Date of Patent: Jan. 24, 2017

(54) NASAL DRUG DELIVERY DEVICE

(71) Applicant: Impel NeuroPharma Inc., Seattle, WA (US)

(72) Inventors: John D. Hoekman, Seattle, WA (US); Michael Hite, Normandy Park, WA (US); Alan Brunelle, Woodinville, WA (US); Joel Relethford, Everett, WA (US); Rodney J. Y. Ho, Mercer Island, WA (US)

(73) Assignee: Impel NeuroPharma Inc., Seattle, WA (US)

( * ) Notice: Subject to any disclaimer, the term of this patent is extended or adjusted under 35 U.S.C. 154(b) by 184 days.

(21) Appl. No.: 14/017,048

(22) Filed: Sep. 3, 2013

(65) Prior Publication Data

US 2014/0014104 A1  Jan. 16, 2014

Related U.S. Application Data

(63) Continuation of application No. PCT/US2012/027754, filed on Mar. 5, 2012.
(Continued)

(51) Int. Cl.
*A61M 15/08* (2006.01)
*A61M 11/02* (2006.01)

(52) U.S. Cl.
CPC .............. *A61M 15/08* (2013.01); *A61M 11/02* (2013.01); *A61M 2202/0468* (2013.01);
(Continued)

(58) Field of Classification Search
CPC .... A61K 2300/00; A61K 31/00; A61K 31/15; A61K 31/352; A61K 31/66; A61K 45/00; A61K 45/06; A61K 47/00; A61K 47/06; A61M 11/00; A61M 15/0086; A61M 15/009; A61M 15/08; A61M 16/10; B01D 11/04; B01D 11/0411; B01J 13/02; B01J 2/02; B65D 83/54; Y10T 29/49405; Y10T 29/4941; Y10T 29/49412
(Continued)

(56) References Cited

U.S. PATENT DOCUMENTS 3,425,414 A  2/1969 Laroche
3,888,253 A  6/1975 Watt et al.
(Continued)

FOREIGN PATENT DOCUMENTS

CN  1293580  5/2001
CN  101815503  8/2010
(Continued)

OTHER PUBLICATIONS

Partial Supplementary European Search Report mailed Mar. 20, 2015 for European patent application No. 12752463.5, 7 pages.
(Continued)

*Primary Examiner* — Annette Dixon
(74) *Attorney, Agent, or Firm* — Lee & Hayes, PLLC

(57) ABSTRACT

A compound delivery device for delivering a plume derived from a propellant and a drug formulation. The drug formulation is in an intranasal dosage form in the form of powder, suspension, dispersion or liquid. The propelled intranasal dosage form is deposited within the olfactory region of the nasal cavity. The drug deposited within the olfactory region is delivered to the brain avoiding the blood-brain-barrier. Hydrofluoroalkane propellant from a pressurized canister is channeled to a diffuser and drug-containing chamber where the intra-nasal dosage form is aerosolized. The aerosolized intra-nasal dosage form passes through a nozzle thus delivering a plume to the olfactory region of a user's nasal cavity.

61 Claims, 24 Drawing Sheets

Related U.S. Application Data

(60) Provisional application No. 61/449,008, filed on Mar. 3, 2011, provisional application No. 61/451,935, filed on Mar. 11, 2011, provisional application No. 61/484,025, filed on May 9, 2011, provisional application No. 61/498,974, filed on Jun. 20, 2011.

(52) U.S. Cl.
CPC . *A61M 2202/064* (2013.01); *A61M 2205/073* (2013.01); *A61M 2205/8225* (2013.01)

(58) Field of Classification Search
USPC ............ 128/200.14, 200.23, 200.24, 203.12, 128/203.15
See application file for complete search history.

(56) References Cited

U.S. PATENT DOCUMENTS

| | | |
|---|---|---|
| 3,906,950 A | 9/1975 | Cocozza |
| 3,908,654 A | 9/1975 | Lhoest et al. |
| 3,921,637 A | 11/1975 | Bennie et al. |
| 3,971,377 A | 7/1976 | Damani |
| 3,998,226 A | 12/1976 | Harris |
| 4,046,146 A | 9/1977 | Rosskamp et al. |
| 4,095,596 A | 6/1978 | Grayson |
| 4,114,615 A | 9/1978 | Wetterlin |
| 4,187,985 A | 2/1980 | Goth |
| 4,227,522 A | 10/1980 | Carris |
| 4,338,931 A | 7/1982 | Cavazza |
| 4,353,365 A | 10/1982 | Hallworth et al. |
| 4,412,573 A | 11/1983 | Zdeb |
| 4,446,990 A | 5/1984 | Stevenson et al. |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,497,944 A | 3/1996 | Weston et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,824,684 A * | 10/1998 | Viner .................... A61K 31/46 514/291 |
| 5,875,776 A | 3/1999 | Vaghefi |
| 5,881,719 A | 3/1999 | Gottenauer et al. |
| 5,899,201 A * | 5/1999 | Schultz ............. A61M 15/0086 128/200.14 |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,092,522 A | 7/2000 | Calvert et al. |
| 6,145,703 A | 11/2000 | Opperman |
| 6,158,676 A | 12/2000 | Hughes |
| 6,180,603 B1 | 1/2001 | Frey, II |
| 6,186,141 B1 | 2/2001 | Pike et al. |
| 6,189,739 B1 | 2/2001 | von Schuckmann |
| 6,211,230 B1 * | 4/2001 | Filbert ................. A61K 31/352 514/454 |
| 6,294,153 B1 | 9/2001 | Modi |
| 6,302,101 B1 | 10/2001 | Py |
| 6,313,093 B1 | 11/2001 | Frey, II |
| 6,347,789 B1 | 2/2002 | Rock |
| 6,367,471 B1 | 4/2002 | Genosar et al. |
| 6,367,473 B1 | 4/2002 | Kafer |
| 6,382,465 B1 | 5/2002 | Greiner-Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Ganan-Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 6,966,990 B2 | 11/2005 | Chattopadhyay et al. |
| 6,991,785 B2 | 1/2006 | Frey, II |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,229,593 B1 * | 6/2007 | Ho .......................... G01N 13/00 422/50 |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,162,921 B2 * | 4/2012 | Flickinger ............. A61M 11/06 128/200.21 |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |

(56) References Cited

U.S. PATENT DOCUMENTS

| | | |
|---|---|---|
| 8,910,629 B2 | 12/2014 | Djupesland et al. |
| 8,925,544 B2 | 1/2015 | Flickinger |
| 8,978,647 B2 | 3/2015 | Djupesland et al. |
| 8,987,199 B2 | 3/2015 | Abdel Maksoud et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 2002/0017294 A1 | 2/2002 | Py |
| 2002/0022001 A1* | 2/2002 | Klecker ............... C07H 21/00 424/1.11 |
| 2002/0054856 A1 | 5/2002 | Jones |
| 2002/0092520 A1 | 7/2002 | Casper et al. |
| 2002/0092521 A1 | 7/2002 | Sullivan et al. |
| 2003/0017119 A1 | 1/2003 | Rabinowitz et al. |
| 2003/0158527 A1 | 8/2003 | Mezzoli |
| 2003/0217748 A1 | 11/2003 | Giroux |
| 2004/0068222 A1 | 4/2004 | Brian |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0018840 A1 | 1/2006 | Lechuga-Ballesteros et al. |
| 2006/0107957 A1 | 5/2006 | Djupesland |
| 2006/0198940 A1 | 9/2006 | McMorrow |
| 2006/0219813 A1 | 10/2006 | Morrison |
| 2006/0240092 A1 | 10/2006 | Breitenkamp et al. |
| 2006/0260606 A1* | 11/2006 | Coifman ............... A61K 9/008 128/200.14 |
| 2006/0260608 A1 | 11/2006 | Armstrong et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Ben-Sasson et al. |
| 2007/0202051 A1 | 8/2007 | Schuschnig |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0230052 A1 | 9/2008 | Montaser |
| 2008/0305077 A1 | 12/2008 | Frey, II et al. |
| 2009/0151722 A1* | 6/2009 | Eason ............... A61M 15/0045 128/203.15 |
| 2009/0257957 A1 | 10/2009 | Burnier et al. |
| 2009/0320832 A1 | 12/2009 | Djupestand |
| 2010/0074959 A1 | 3/2010 | Hansom et al. |
| 2010/0143503 A1* | 6/2010 | Szabo ............... A61K 33/00 424/706 |
| 2011/0048411 A1 | 3/2011 | Walker |
| 2011/0053859 A1 | 3/2011 | Deadwyler et al. |
| 2011/0088690 A1 | 4/2011 | Djupesland et al. |
| 2011/0159519 A1* | 6/2011 | Schmidt ............ A61K 49/0021 435/7.2 |
| 2012/0195959 A1 | 8/2012 | Ishii |
| 2012/0222675 A1 | 9/2012 | Dunne et al. |
| 2014/0083424 A1 | 3/2014 | Hoekman et al. |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0216823 A1 | 8/2015 | Chatterjee |
| 2015/0216993 A1* | 8/2015 | Baker, Jr. ......... A61K 47/48207 424/78.17 |
| 2015/0258178 A1 | 9/2015 | Gong |
| 2016/0101245 A1 | 4/2016 | Hoekman et al. |
| 2016/0228433 A1 | 8/2016 | Haruta et al. |

FOREIGN PATENT DOCUMENTS

| | | |
|---|---|---|
| DE | 19518580 A1 | 11/1996 |
| DE | 102013100473 A1 | 7/2014 |
| EA | 013892 | 8/2010 |
| EA | 011654 | 4/2016 |
| EP | 1165044 A2 | 1/2002 |
| GB | 806284 A | 12/1958 |
| GB | 1517642 A | 7/1978 |
| JP | H08322934 A | 12/1996 |
| JP | 2002506696 | 3/2002 |
| JP | 2003210582 | 7/2003 |
| JP | 2008546634 | 12/2008 |
| RU | 2100035 | 12/1997 |
| RU | 2319513 | 3/2008 |
| WO | WO8601731 A1 | 3/1986 |
| WO | WO9913930 A1 | 3/1999 |
| WO | WO9947195 | 9/1999 |
| WO | WO0054887 A1 | 9/2000 |
| WO | W00136033 A2 | 5/2001 |
| WO | WO0209707 | 2/2002 |
| WO | WO02056948 | 7/2002 |
| WO | WO2007/012853 A1 | 2/2007 |
| WO | WO2008/059385 A2 | 5/2008 |
| WO | WO2009100383 A2 | 8/2009 |
| WO | WO2012024595 A3 | 5/2012 |
| WO | WO2012072542 | 6/2012 |
| WO | WO2012119153 | 9/2012 |

OTHER PUBLICATIONS

Translated Chinese Office Action mailed May 14, 2015 for Chinese patent application No. 201280021497.4, a counterpart foreign application of U.S. Appl. No. 14/017,048, 23 pages.

The PCT Search Report and Written Opinion mailed Jun. 20, 2012 for PCT application No. PCT/US12/27754, 7 pages.

Hoekman et al, "Enhanced Analgesic Responses After Preferential Delivery of Morphine and Fentanyl to the Olfactory Epithelium in Rats", Anesthesia & Analygesia, Sep. 2011, vol. 113, No. 3, 11 pgs.

Merkus, "Direct Access of Drugs to the Human Brain after Intranasal Drug Administration?", Neurology 60, May 2003, 3 pgs.

Westin et al, "Direct Nose-to-Brain Transfer of Morphine after Nasal Administration to Rats", Pharmaceutical Research, vol. 23, No. 3, Mar. 2006 , 8 pgs.

Westin et al, "Transfer of Morphine Along the Olfactory Pathway to the Central Nervous System after Nasal Administration to Rodents", European Journal of Pharmaceutical Sciences, vol. 24, Jan. 2005, pp. 565-573.

The PCT Search Report and Written Opinion mailed Aug. 14, 2014 for PCT application No. PCT/US14/35711, 13 pages.

The Extended European Search Report mailed Jul. 8, 2015 for European patent application No. 12752463.5, 13 pages.

The Australian Office Action mailed Sep. 22, 2015 for Australian patent application No. 2012223160, a counterpart foreign application of U.S. Appl. No. 14/017,048, 3 pages.

Translated Chinese Office Action mailed Nov. 27, 2015 for Chinese patent application No. 201280021497.4, a counterpart foreign application of U.S. Appl. No. 20 pages.

Translated Japanese Office Action mailed Jan. 5, 2016 for Japanese Patent Application No. 2013-556677, a counterpart foreign application of U.S. Appl. No. 14/017,048, 10 pages.

Translated Russian Office Action mailed Jan. 21, 2016 for Russian patent application No. 2013144395, a counterpart foreign application of U.S. Appl. No. 14/017,048, 6 pages.

Banks, et al., "Brain Uptake of the Glucagon-Like Peptide-1 Antagonist Exendin(9-39) After Intranasal Administration", J. Pharmacol. Exp. Ther., 2004, vol. 309 (2), pp. 469-475.

Guo, et al., "Evaluation of Impaction Force of Nasal Sprays and Metered-Dose Inhalers Using the Texture Analyser", J. Pharm. Sci., 2009, vol. 98 (8), pp. 2799-2806.

Henry, et al., "A Pharmacokinetic Study of Midazolam in Dogs: Nasal Drop vs. Atomizer Administration", Pediatr. Dent., 1998, vol. 20 (5), pp. 321-326.

(56) References Cited

OTHER PUBLICATIONS

Liu, et al., "Creation of a Standardized Geometry of the Human Nasal Cavity", J. Appl. Physiol., 2009, vol. 106 (3), pp. 784-795.
Pardridge, "Targeting Neurotherapeutic Agents through the Blood-Brain Barrier", Arch. Neurol., 2002, vol. 59 (1), pp. 35-40.
Pardridge, "The Blood-Brain Barrier: Bottleneck in Brain Drug Development", NeuroRx., 2005, vol. 2 (1), pp. 3-14.
Pardridge, "The Blood-Brain Barrier and Neurotherapeutics", NeuroRx., 2005, vol. 2 (1), pp. 1-2.
The Australian Office Action mailed Mar. 23, 2016 for Australian patent application No. 2012223160, a counterpart foreign application of U.S. Appl. No. 14/017,048, 3 pages.
Ding, et al., "Olfactory Mucosa: Composition, Enzymatic Localization, and Metabolism", Handbook of Olfaction and Gustation, 2nd Ed (Doty RL, Ed), 2003, pp. 51-73.
Letrent, et al., "Effects of a Potent and Specific P-Glycoprotein Inhibitor on the Blood-Brain Barrier Distribution and Antinociceptive Effect of Morphine in the Rat", Drug Metab. Dispos., 1991, vol. 27 (7), pp. 827-834.
Mathison, et al., "Nasal Route for Direct Delivery of Solutes to the Central Nervous System: Fact or Fiction?", J. Drug Target., 1998, vol. 5 (6), pp. 415-441.
Morrison, et al., "Morphology of the Human Olfactory Epithelium", J. Comp. Neurol., 1990, vol. 297 (1), pp. 1-13.
Petroianu, et al., "New K-Oximes (K-27 and K-48) in Comparison with Obidoxime (LuH-6), HI-6, Trimedoxime (TMB-4), and Pralidoxime (2-PAM): Survival in Rats Exposed IP to the Organophosphate Paraoxon", Toxicol. Mech. Methods, 2007, vol. 17 (7), pp. 401-408.
Sakane, et al., "Transport of Cephalexin to the Cerebrospinal Fluid Directly from the Nasal Cavity", J. Pharm. Pharmacol., 1991, vol. 43 (6), pp. 449-451.
Thiermann, et al., "Pharmacokinetics of Obidoxime in Patients Poisoned with Organophosphorus Compounds" Toxicol. Lett., 2010, vol. 197 (3), pp. 236-242.
Zhang, et al., "Preparation of Nimodipine-Loaded Microemulsion for Intranasal Delivery and Evaluation on the Targeting Efficiency to the Brain", Int. J. Pharm., 2004, vol. 275 (1-2), pp. 85-96.
Buursma, et al., "[18F]FHPG Positron Emission Tomography for Detection of Herpes Simplex Virus (HSV) in Experimental HSV Encephalitis", J Virol. Jun. 2005;79(12):7721-7, abstract, found on May 13, 2016 in PubMed PMID: 15919924.
Deadwyler, et al., "Systemic and Nasal Delivery of Orexin-A (Hypocretin-1 Reduces the Effects of Sleep Deprivation on Cognitive Performance in Nonhuman Primates)", J Neurosci. Dec. 26, 2007;27(52): 14239-47, abstract, found on May 13, 2016 in PubMed PMID: 18160631.
Domino, et al., "Effect of Nicotine on Regional Cerebral Glucose Metabolism in Awake Resting Tobacco Smokers", Neuroscience. 2000;101(2):277-82, abstract, found on May 13, 2016 in PubMed PMID: 11074150.
Gurevich, Development of Intranasal Medicine Delivery Systems, Quality Clinical Practice, No. 1, 2002, pp. 2-5.
Hanson, et al., "Intanasal Deferoxime Provides Increased Brain Exposure and Significant Protection in Rat Ischemic Stroke", J Pharmacol Exp Ther. Sep. 2009; 330(3):679-86, Full text, found on Jan. 15, 2016 in PubMed PMCID: PMC2729791.
Interferon Alpha (Interferon Alfa): Instruction, and the Use of Formula, posted in Internet: <URL rlsnet.ru/mnn_index_id_649. htm> Jul. 24, 2009; the date of posting is confirmed in Internet-archive: web.archive.org/web/20090724182541/rlsnet.ru/mnn_index_id_649.htm>).
Lin, et al., "High Uptake in Schneiderian Papillomas of the Maxillary Sinus on Positron-Emission Tomography Using Fluorodeoxyglucose", AJNR Am J Neuroradiol. Feb. 2009;30(2):428-30, abstract, found on May 13, 2016 in PubMed PMID: 18768722.

Russian Office Action mailed May 13, 2016 for Russian patent application No. 2013144395, a counterpart foreign application of U.S. Appl. No. 14/017,048, 12 pages.
Taylor, et al., "Imaging Allergen-Invoked Airway Inflammation in Atopic Asthma with [18F]- Fluorodeoxyglucose and Positron Emission Tomography", Lancet, 1996, vol. 347, pp. 937-940.
Appasaheb, et al., "Review on Intranasal Drug Delivery System", Journal of Advanced Pharmacy Education and Research, vol. 3, Issue 4, Oct. 2013, 14 pages.
Baron, "Orally Inhaled Dihydroergotamine; Reviving and Improving a Classic", Future Neurology, May 2011, 11 pages.
Constantino, et al., "Intranasal administration of acetylcholinesterase inhibitors", BMC Neuroscience, Dec. 10, 2008, 3 pages.
EP Search Report for 09707800.0 mailed Jul. 1, 2015, 12 pages.
EP Search Report for 11818832.5 mailed Sep. 24, 2014, 6 pages.
Hanson, et al., "Intranasal delivery of growth differentiation factor 5 to the central nervous system", Drug Delivery, 19 (3): 149-54, Feb. 2012, 7 pages.
Hoekman, J.D., "The Impact of Enhanced Olfactory Deposition and Retention on Direct Nose-to-Brain Drug Delivery", UMI Dissertation Publishing, Apr. 11, 2011, 181 pages.
International Search Report for PCT/US/2009/033468 dated Dec. 2, 2009, 5 pages.
Kumar, et al., "Nasal Drug Delivery: A Potential Route for Brain Targeting" The Pharma Innovation Journal, vol. 2, No. 1, Mar. 2013. 9 pages.
Ozsoy, et al., "Nasal Delivery of High Molecular Weight Drugs", Molecules Journal, Sep. 23, 2009, 26 pages.
Parvathi, "Intranasal Drug Delivery to Brain: An Overview," published in the International Journal of Research in Pharmacy and Chemistry 2012, 2(3), 7 pages.
PCT Search Report and Written Opinion mailed Mar. 27, 2012 for PCT application No. PCT/US11/48435, 14 pages.
Renner, et al., "Intranasal delivery of growth differentiation factor 5 to the central nervous system," Drug Delivery, Feb. 2012, 7 pages.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, vol. 39, No. 12, 8 pages.
Talegaonkar, et al., "Intranasal delivery: An approach to bypass the blook brain barrier", Indian J Pharmacol, Jun. 2004, vol. 36, Issue 3, 8 pages.
Westin et al, "Direct Nose to Brain Transfer of Morphine After Nasal Administration to Rats", Pharmaceutical Research, vol. 23, No. 3, Mar. 2006, 8 pgs.
Westin, "Olfactory Transfer of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yiman, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medecine, 3(1), Jan. 2008, 4 pages.
Zhang, et al, "The brain targeting efficiency following nasally applied MPEG-PLA nanoparticles in rats", Journal of Drug Targeting, Jun. 2006, 11 pages.
EP Ofice Action for application 14727320.5, mailed Nov. 9, 2016, 6 pages.
Ling, et al., "The OxyArm—a new minimal contact oxygen delivery system for mouth or nose breathing" Can J Anaesth. Mar. 2002, 49(3):297-301, abstract, found on Oct. 12, 2016 in PubMed PMID: 118650.

\* cited by examiner

NASAL DRUG DELIVERY DEVICE

CROSS REFERENCE TO RELATED APPLICATIONS

This application is a continuation of an international patent application PCT/US12/27754, filed Mar. 5, 2012, which claims priority to U.S. Ser. No. 61/449,008, filed Mar. 3, 2011, U.S. Ser. No. 61/451,935, filed Mar. 11, 2011, U.S. Ser. No. 61/484,025, filed May 9, 2011, and U.S. Ser. No. 61/498,974, filed Jun. 20, 2011, the entire contents of which are hereby incorporated by reference herein in their entirety.

STATEMENT CONCERNING GOVERNMENT INTEREST

This invention was made with U.S. government support pursuant to U.S. Army SBIR grant W81XWH-10-C-0238. The Government may have certain rights in this application.

BACKGROUND

The central nervous system (CNS) includes the brain, the brain stem, and the spinal cord. The CNS is isolated from the external world by several membranes that both cushion and protect the brain, the brain stem, and the spinal cord. For example, the membranes that form the blood-brain barrier (BBB) protect the brain from certain contents of the blood. The blood-cerebrospinal fluid barrier (BCSFB) protects other portions of the CNS from many chemicals and microbes.

Traditional methods for delivering compounds to the CNS are typically invasive. For example, a pump implanted in the skull, such as an intracerebroventricular pump, can deliver a variety of compounds to the brain. However, implanting such a pump requires brain surgery, which can entail a variety of serious complications. Certain compounds, for example epidural painkillers, can be injected directly through the protective membrane into the CNS. However, such injection is impractical for most compounds.

Intranasal administration has traditionally focused on the distribution of drug solutions as a mist for topical delivery to the nasal epithelium. Because of the nasal cavity's easily accessed vascular bed, nasal administration of medications has focused the delivery of medications either locally to the nasal cavity or directly to the blood stream.

Much of the current brain research is focused on the enhancement of the drug being delivered to the brain by various formulations. The traditional approaches to improve uptake of compounds to the brain by formulation enhancement include (1) mucoadhesive formulations; 2) penetration enhancers; 3) liposomes; 4) vasoconstrictors; and 5) nanoparticles. Examples of various compounds with have enhanced formulations include various cytokines, for example, tumor necrosis factors, interleukins, and interferons discussed in U.S. Pat. No. 6,991,785 and growth and differentiation factor-5 (GDF-5) and related proteins discussed in US Publication No. 20100074959.

Targeting of drugs to the central nervous system (CNS) is a challenging task. A great number of drugs, including biotechnology products, are candidates for treatment of CNS diseases, but drug delivery is a problem for brain targeting. A limitation in the treatment of brain tumors is that less than 1% of most therapeutic agents administered systemically are able to cross the BBB. The transport of small molecules across the BBB is the exception rather than the rule, and 98% of all small molecules do not cross the BBB (Pardride, NeuroRx. 2005 January; 2(1): 1-2. 2005); approximately 100% of large-molecule drugs or genes do not cross the BBB (Pardride, NeuroRx. 2005 January; 2(1): 1-2. 2005). The BBB allows small (about less than 500 Da), lipophilic molecules from the bloodstream to enter the CNS (Pardridge, Arch Neurol. 2002; 59:35-40). Many larger therapeutic agents are prevented from reaching the brain for treating CNS disorders such as but not limited to Parkinson's disease, Alzheimer's disease, depression, stroke, and epilepsy (Pardridge, NeuroRx. 2005 January; 2(1): 3-14). Disorders including autism, lysosomal storage disorders, fragile X syndrome, ataxis, and blindness, are serious disorders where there is little effective treatment. In many of these cases, the gene underlying the disease is known, but BBB delivery is the rate-limiting problem in gene therapy or enzyme replacement therapy, and no therapeutics have been developed. Drug delivery of therapeutic compounds, for example proteins, faces several challenges because of their instability, high enzymatic metabolism, low gastrointestinal absorption, rapid renal elimination, and potential immunogenicity.

There is a need for devices that can deliver compounds to the upper nasal cavity for direct nose-to-brain delivery. Certain existing nasal drug delivery devices do not adequately propel the drug from the device. Inconsistent propulsion of drug due to inconsistent user actuation is also far from optimal. Still further, the plume generated by such existing devices is too wide. Even further, some drug products do not readily mix and/or stay suspended with propellants in a MDI type device. Certain existing nasal drug devices rely on circumferential velocity to propel medicaments to the olfactory epithelium. Traditional circumferential devices result in a lower percentage of compound deposited on the olfactory epithelium. A circumferential component in the aerosol plume tends to result in a wider spray plume with a portion of the aerosol particles targeted to the sides of the nasal cavity in the lower part of the nasal cavity.

Better mechanisms for administering desired agents to the brain, brain stem, and/or spinal cord are needed.

SUMMARY

A device for delivering a compound to the olfactory region of the nasal cavity is described including a canister capable of containing a propellant, a diffuser in communication with the canister, a compound chamber in communication with the diffuser, and a nozzle in communication with the compound chamber, wherein the device is capable of delivering the compound to the olfactory region of the nasal cavity.

In one aspect, the device includes a canister that is pressurized.

In another aspect, the propellant includes HFA, nitrogen, or CFC.

In another aspect, the device includes a compound chamber containing a drug or an imaging agent.

In yet another aspect, the drug is an oxime.

In yet another aspect, the diffuser is a frit.

In yet another aspect, the imaging agent is FDG or FLT.

In yet another aspect, the device includes a propellant, where the propellant is a pressurized liquid.

In yet another aspect, the pressurized liquid is HFA.

In another aspect, the pressurized liquid HFA is released from the canister and comes into contact with the diffuser, whereby the diffuser converts the pressurized liquid HFA to gaseous HFA.

In another aspect, the diffuser converts a minority of the pressurized liquid HFA to gaseous HFA.

In a further aspect, the diffuser converts a majority of the pressurized liquid HFA to gaseous HFA.

In yet another aspect, the device delivers at least 62.6% of the compound to the olfactory region.

In yet another aspect, the he device delivers greater than 64.2% of the compound to the olfactory region.

In another aspect, the device delivers at least 64.3% of the compound to the olfactory region.

In yet another aspect, the device includes a canister where the canister is a syringe, syrette, or barrel.

In yet another aspect, the compound is not an imaging agent.

In further aspect, the compound is not FDG.

In one aspect, the drug is in the form of a liquid suspension, a liquid dispersion, a powder, or an aqueous solution.

In yet another aspect, the device further includes an aiming guide.

In yet another aspect, the aiming guide aides in positioning of the nozzle of the device at the user's olfactory region.

In yet another aspect, the devices further includes an insertion port in communication with the compound chamber.

In yet another aspect, the device further includes an indicator provided to alert the user to the length or amount of a capsule's insertion into the user's nasal cavity.

In one aspect, the diffuser is porous.

In another aspect, the diffuser is heterogeneously porous.

In another aspect, the diffuser is homogenously porous.

In another aspect, the diffuser is extended.

In yet another aspect, the diffuser is a disk-shaped member including conical shaped members having distal apertures.

In yet another aspect, the canister is a metered dose inhaler.

In another embodiment, a device for delivering a compound is described including a canister capable of containing a propellant, a diffuser in communication with the canister, a compound chamber in communication with the diffuser, and a nozzle in communication with the compound chamber, where the device is capable of delivering the compound to ear, skin, buccal cavity, or eyes.

In another embodiment, a method is described for delivering drug to the olfactory region of the nasal cavity including providing a canister capable of containing a propellant, a diffuser in communication with the canister, a compound chamber in communication with the diffuser, and a nozzle in communication with the compound chamber, where when actuated the device is capable of delivering the compound to the olfactory region of the nasal cavity.

In one aspect, the method includes the delivery of a drug for the treatment of an infectious disease, oncology, or immunological disease.

In one aspect, the method includes actuating the device to deliver propellant from the canister, whereby the diffuser diffuses the liquid propellant from the canister to a gaseous propellant, the gaseous propellant contacts the compound in the compound chamber and the compound and gaseous propellant exits the nozzle of the device.

In another aspect of the method, the diffuser converts a minority of the pressurized liquid HFA to gaseous HFA.

In another aspect of the method, the diffuser converts a majority of the pressurized liquid HFA to gaseous HFA.

In yet another aspect of the method, at least 64.2% of the compound is delivered to the olfactory region.

In yet another aspect of the method, greater than 64.2% of the compound is delivered to the olfactory region.

In another aspect of the method, the compound is a drug or diagnostic agent.

In another aspect of the method, the compound is a drug.

In yet another aspect of the method, the diagnostic agent is an imaging agent.

In yet another aspect of the method, the drug is an oxime.

In yet another aspect of the method, the imaging agent is fluorodeoxyglucose or fluorothymidine.

In yet another aspect of the method, the compound is not fluorodeoxyglucose.

In yet another aspect of the method, the compound is not an imaging agent.

In yet another aspect of the method, the drug is in the form of a liquid suspension, a liquid dispersion, a powder, liposome, or an aqueous solution and combinations thereof.

In yet another aspect of the method, the device includes one or more aiming guides.

In yet another aspect of the method, the aiming guide assists in the positioning of the nozzle of the device at the user's olfactory region.

In another aspect of the method, the device includes an insertion port in communication with the compound chamber.

In an aspect of the method, the device includes an indicator provided to alert the user to the depth of insertion of the device into the user's nasal cavity.

In another aspect of the method, the diffuser is porous.

In another aspect of the method, the diffuser is heterogeneously porous.

In another aspect of the method, the diffuser is homogenously porous.

In an aspect of the method, the diffuser is extended.

In another aspect of the method, the diffuser is a disk-shaped member including conical shaped members having distal apertures.

In an aspect of the method, the canister is a metered dose inhaler.

In another embodiment, an intranasal formulation of an oxime for use in treating exposure to an organophosphate is described.

In yet another embodiment, a method is described for delivering an oxime across the blood brain barrier to a subject in need thereof including administering to the subject a therapeutically effective dosage of an oxime, wherein the dosage is delivered to the upper olfactory region of the nasal cavity.

In one aspect of the method, the therapeutically effective amount of an oxime administered to the user is within the range of about 0.001 mg/kg to about 100 mg/kg.

In another aspect of the method, the therapeutically effective amount of an oxime administered to the user is within the range of about 0.01 mg/kg to about 10 mg/kg.

In yet another aspect of the method, the therapeutically effective amount of an oxime administered to the user is within the range of about 0.1 mg/kg to about 1 mg/kg.

In yet another aspect, the method described for delivering an oxime is for treatment of organophosphate exposure.

In another embodiment, a method of delivering an oxime intranasally to a user is described including providing a nasal dosage form of the oxime, propelling the nasal dosage form with a propellant, and delivering the nasal dosage form to the nasal cavity of the user, so that the oxime is delivered to the nasal cavity and subsequently to the central nervous system and/or brain of the user.

In one aspect, the oxime delivered includes 2-PAM, MMB4, HI6, TMB4 or Hlo7 and combinations thereof.

In another aspect, the nasal dosage form of the oxime is a powder, an aqueous solution, a suspension or a lipid containing product and combinations thereof.

In another aspect, the user has been exposed to an organophosphate drug including sarin, tabun, soman, Russian VX or diisopropylfluorophosphate and combinations thereof.

In another aspect, a majority of the oxime in nasal dosage form is deposited within the nasal cavity.

In another aspect, a nasal dosage form of a muscarinic receptor agonist or a muscarinic receptor antagonist is delivered intranasally.

In yet another aspect, a nasal dosage form of atropine or scopolamine or combinations thereof is provided intranasaly.

In yet another aspect, a nasal dosage form a benzodiazepine antagonist is provided intranasally.

In yet another aspect, the benzodiazepine antagonist includes diazepam, midazolam or lorazepam or combinations thereof.

In yet another aspect, the nasal dosage form is a benzodiazepine antagonist, a muscarinic receptor agonist or a muscarinic receptor antagonist or combinations thereof.

In yet another aspect, the intranasal dosage form includes diazepam, midazolam, lorazepam, atropine or scopolamine or combinations thereof.

In yet another aspect, the nasal dosage form is delivered to the nasal cavity of the user exposed to an organophosphate.

In another aspect, the nasal dosage form is delivered to the nasal cavity of the user before the exposure to an organophosphate.

In yet another aspect, the nasal dosage form is delivered to the nasal cavity of the user after the exposure to an organophosphate.

In yet another aspect, exposure to the oxime increases oxime exposure to the CNS. In yet further aspects, at least 53% of the oxime is directly transported (DTP) to the brain.

The invention will best be understood by reference to the following detailed description of various embodiments, taken in conjunction with the accompanying drawings. The discussion below is descriptive, illustrative and exemplary and is not to be taken as limiting the scope defined by any appended claims.

BRIEF DESCRIPTION OF DRAWINGS

FIG. 16 B shows a cross section of the device of FIG. 16 A.

FIG. 22 shows a majority of the spray to be in the olfactory region.

DETAILED DESCRIPTION OF THE EMBODIMENTS

Figure 1:
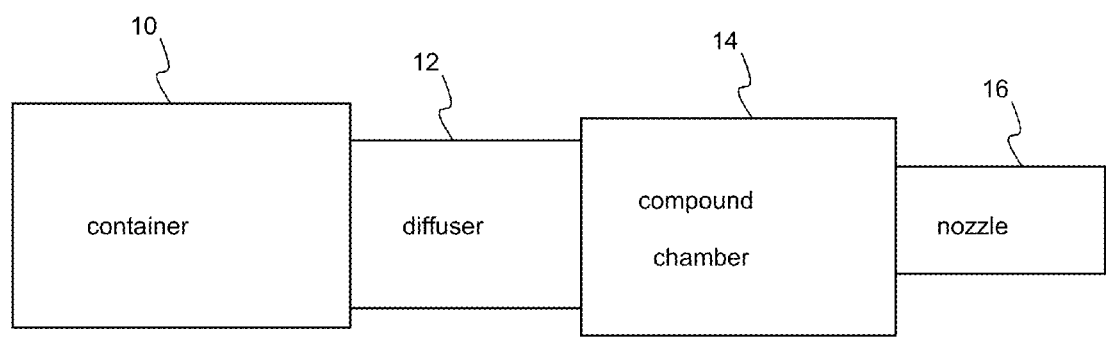
FIG. 1 is a schematic drawing of one embodiment of the invention.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise:

As used herein the specification, "a" or "an" may mean one or more.

A "diagnostic agent" refers to and encompasses an atom, molecule, or compound that is useful in diagnosing a disease. Diagnostic agents include, but are not limited to, radioisotopes, dyes, contrast agents, fluorescent compounds or molecules and enhancing agents (e.g., paramagnetic ions). A non-radioactive diagnostic agent is a contrast agent suitable for magnetic resonance imaging, computed tomography or ultrasound. The diagnostic agent can be used to perform positron emission tomography (PET), MRI, X-ray, CT, ultrasound, operative, intravascular, laparoscopic, or endoscopic procedure.

A "diffuser" refers to and encompasses a device for dispersing or deflecting a compound in various directions.

A "frit" shall refer to and encompass a porous member or filter.

An "imaging agent" refers to and encompasses an atom, molecule or compound that is useful in detecting physical changes or produces images of internal body tissues. In some aspects, the imaging agent may be a diagnostic agent.

A "propellant" shall refer to and encompass a compound that acts as a vehicle for creating propulsion or thrust.

The term "therapeutically effective amount" refers to and encompasses an amount of a drug effective to treat a disease or disorder in a mammal. In one aspect, the therapeutically effective amount refers to a target CNS concentration that has been shown to be effective in, for example, slowing disease progression. Efficacy can be measured in conventional ways, depending on the condition to be treated.

The term "treatment" and "treat", and the like, refers to and encompasses therapeutic or suppressive measures for a disease or disorder leading to any clinically desirable or beneficial effect, including, but not limited to, alleviation or relief of one or more symptoms, regression, slowing or cessation of progression of the disease or disorder. Treatment can be evidenced as a decrease in the severity of a symptom, the number of symptoms, or frequency of relapse.

A "user" or "subject" shall refer to and encompass a human or other animal. For example, the animal may be a primate or a non primate and may include a rabbit, bovine, equine, pig, rat, mouse, dog or cat.

The device may be used in treatment, prevention, palliative care for humans and veterinary purposes. The device may be used in research and industrial uses. For example, the device may be used to deposit compound in agricultural settings.

When trade names are used herein, applicants intend to independently include the trade name product formulation, the generic drug, and the active pharmaceutical ingredient(s) of the trade name product.

For clarity of disclosure, and not by way of limitation, the detailed description of the invention is divided into the subsections which follow.

Intranasal administration of compounds offers several advantages over traditional surgical, intravenous or oral routes for administration across the blood brain barrier (BBB). Intranasal administration to the olfactory region avoids gastrointestinal destruction and hepatic first pass metabolism, such as destruction of drugs by liver enzymes, allowing more drug to be cost-effectively, rapidly, and predictably bioavailable than if it were administered orally. Intranasal administration provides ease, convenience and safety. Intranasal drug administration is generally painless (taking into consideration that pain may be a subjective measurement which varies by patient) and does not require sterile technique, intravenous catheters or other invasive devices, and is generally immediately and readily available for all patients. Intranasal administration can rapidly achieve therapeutic brain and spinal cord drug concentrations.

Nasally administered compounds contact the upper olfactory region and molecular transport occurs directly across this tissue and into compartments of the central nervous system. (Henry, R. J., et al., Pediatr Dent, 1998. 20(5): p. 321-6; Sakane, T., et al., J Pharm Pharmacol, 1991. 43(6): p. 449-51; Banks, W. A., et al., J Pharmacol Exp Ther, 2004. 309(2): p. 469-75; Westin, et al., Pharm Res, 2006. 23(3): p. 565-72). The olfactory mucosa is located in the upper nasal cavity, just below the cribriform plate of the skull. It contains olfactory cells which traverse the cribriform plate and extend up into the cranial cavity. When compounds come in contact with this specialized mucosa, they are rapidly transported directly into the brain, they bypass the BBB, and are rapidly transported directly into the central nervous system, often faster than if the compound is given intravenously.

The olfactory mucosa includes the olfactory epithelium. The olfactory epithelium is located at the top of the nose between the superior turbinate and the roof of the nasal cavity, just beneath the cribriform plate of the ethmoid bone. In humans, it covers about 10 to about 20 cm2, or about 8% of the total nasal surface area, and is composed of four main cell types: epithelial cells, olfactory receptor neurons, supporting cells, and basal cells. (Mathison S. et al., (1998) Journal of Drug Targeting 5: 415-441). Although 3% of the nasal cavity is occupied by olfactory epithelium (Morrison and Costanzo, 1990), this route is direct, since the olfactory neurons do not have a synapse between the receptive element and the afferent path (Ding and Dahl, 2003). The olfactory epithelium is more than twice the depth of the respiratory epithelium, with the olfactory nerve cell bodies typically located in the middle and deeper regions of the epithelium while nuclei of the supporting cells are organized in a single layer closer to the mucosal surface. Tight junctions exist between the supporting cells and between the supporting cells and olfactory nerve cells. Morrison E. E, et al. (1992) Journal of Comparative Neurology 297(1): 1-13.

When a nasal drug formulation is delivered deep and high enough into the nasal cavity, the olfactory mucosa is reached and drug transport into the brain and/or CSF via the olfactory receptor neurons occurs. The transfer of compounds from the nose to the brain is referred to as the nose-brain pathway. The nose-brain pathway has implications when centrally acting medications such as but not limited to sedatives, anti-seizure drugs and opiates are delivered nasally. The present device allows for delivery via the nose-brain pathway allowing for nearly immediate delivery of nasal medications to the central nervous system and brain, by-passing the blood brain barrier.

The current challenge in nose-to-brain drug delivery is also due to the complex architecture of the nose, which is naturally designed to channel drugs into the lower nasal airway toward the lungs making it difficult for drugs to reach the olfactory region. Most of the drug dispensed from traditional nasal devices such as sprayers or pumps is subjected to the natural air movement in the nasal cavity towards the esophagus. The majority of the spray dispensed from traditional devices encounters the natural downward airflow displacement within the nasal cavity. The remaining fraction from traditional devices is found in the respiratory epithelium and cleared by the mucocilliary clearance mechanism or absorbed into the blood stream. While nasal catheter instillation and nose drops are less impacted by this natural downward air movement, it requires subjects to be in a supine position, is often associated with user discomfort, and is not optimal for frequent clinical administration.

Moreover, a reservoir of residual air exists at the top of the nasal cavity that is not removed during normal respiration; thus remaining in the olfactory region and acting as a barrier to deposition. This residual air must be displaced in order to deliver aerosolized drug to the olfactory epithelium in the upper nasal cavity in a consistent manner. The device described herein delivers a majority of the aerosolized drug to the upper part of the nasal cavity to increase exposure of the drug at the olfactory epithelium, a site of nose-to-brain pathway, by both avoiding the natural downward air movement and displacing the residual air of the upper nasal cavity.

The device herein advantageously and consistently deposits a large fraction of dose into the more distal parts of the nasal cavity such as the olfactory region. A drug product (also referred to herein as drug formulation or nasal dosage form) is propelled from the device with a velocity into the nasal cavity.

FIG. 1 shows one embodiment of the device where a container 10 contains a propellant. The propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and the like HFA's. In one aspect, the propellant is liquid HFA. In another aspect, the propellant is gaseous HFA. Additional examples of suitable propellants include nitrogen or choloroflourocarbons (CFC). Additionally, propellants may be pressurized air (e.g. ambient air). The container 10 may be a conventional metered dose inhaler (MDI) device that includes a pressurized canister, metering valve (including stem) to meter the propellant upon actuation. In certain aspects, the propellant is not metered upon actuation. In one aspect, the container 10 does not contain drug. In another aspect, the container includes a propellant and a drug.

The container 10 is in communication with a diffuser 12. For example, when the diffuser 12 is in communication with the container 10, "communication" shall refer to and encompass congruousness or fluid communication. The propellant from the container 10 is diffused via the diffuser 12. In one aspect, a majority of the propellant is diffused via the diffuser 12. In another aspect, a minority of the propellant is diffused via the diffuser 12. Majority refers to and encompasses at least 50 percent. Minority refers to and encompasses less than 50 percent. In another aspect, at least about 10%, 15%, 20%, 25%, 30%, 35%, 40%, 45%, 50%, 55%, 60%, 65%, 70%, 75%, 80%, 85%, 90%, 95%, 99% or about 100%, inclusive of endpoints, of the propellant is diffused via the diffuser 12. The diffuser 12 is in communication with the compound chamber 14. The compound chamber 14 is capable of holding a compound, such as but not limited to a drug or/and a diagnostic agent. In one aspect, the diagnostic agent is an imaging agent. In an example, the imaging agent is fluorodeoxyglucose (FDG) or fluorothymidine (FLT). In another aspect, the compound is a drug. In another aspect, the compound is not an imaging agent. In one aspect, the compound is a liquid. In another aspect, the compound is a powder. In yet another aspect, the compound is an intranasal formulation of a drug in a liquid or powdered state. The intranasal formulation may contain suitable intranasal carriers and excipients known in the art.

The propellant in the container 10 acts as a vehicle to deliver propulsion or thrust to expel from the compound chamber 14 the compound. The compound chamber 14 is in communication with a nozzle 16. The propulsion or thrust from the propellant is capable of expelling the compound from the compound chamber 14 and nozzle 16 when in communication with the compound chamber 14.

In one aspect, when the MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 and about 200 inclusive of endpoints, of liquid propellant.

Figure 2:
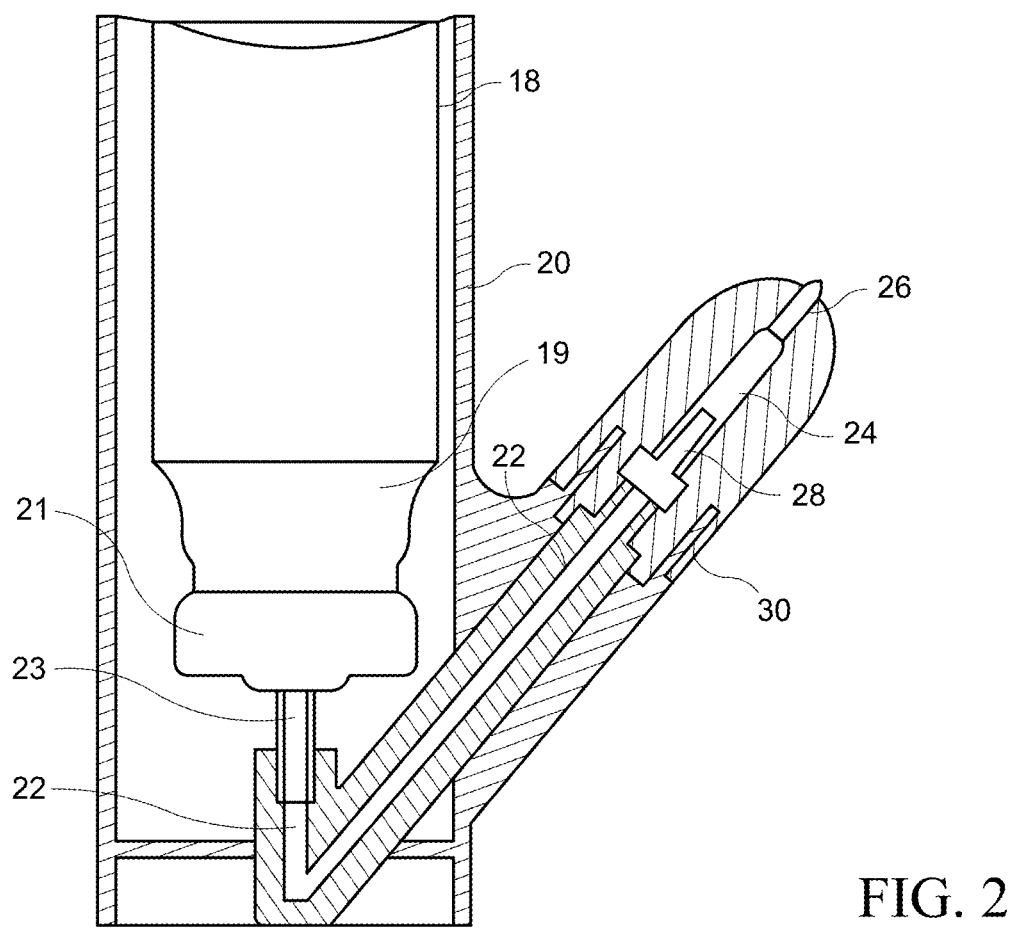
FIG. 2 shows an embodiment of the invention.

FIG. 2 shows one embodiment of the device. The actuator body 20 houses a container 10, in one aspect the container 10 is a metered dose inhaler that includes a propellant canister 18 having a neck 19 and a metering valve assembly 21. A valve stem 23 is in communication with a connection channel 22. The propellant exiting the valve stem 23 is a fluid. The fluid may be liquid, gas, or a combination. A diffuser 28 is in communication with the propellant exiting the container 10 and the compound chamber 14.

Propellant exiting the container 10 comes into contact with the diffuser 28. The diffuser 28 is capable of converting liquid propellant exiting the container 10 into gaseous propellant. In one aspect, the diffuser 28 is capable of converting all or a majority of the liquid propellant into gaseous propellant. In another aspect, the diffuser is capable of converting a minority of the liquid propellant into gaseous propellant. Majority refers to and encompasses at least 50 percent.

Minority refers to and encompasses less than 50 percent. In another aspect, at least about 10%, 15%, 20%, 25%, 30%, 35%, 40%, 45%, 50%, 55%, 60%, 65%, 70%, 75%, 80%, 85%, 90%, 95%, 99° A or about 100%, inclusive of endpoints, of the liquid propellant is converted into gaseous propellant. Following contact with the diffuser 28, the diffused propellant comes into contact with the compound in the compound chamber 14. The diffused propellant and the compound come into contact with each other as the propellant propels the compound in the compound chamber 114. The nozzle 16 is in fluid communication with the compound chamber 14. The compound is propelled by the diffused propellant into communication with the nozzle 16. The propellant propels the compound to be expelled via the distal end of the nozzle 16. Exiting from the nozzle 16 is compound, propellant, or a combination thereof.

In some aspects, the diffuser 28 functions to convert propellant from a liquid to a gas. In other aspects, the diffuser 28 functions to prevent the compound contained in the compound chamber 14 from coming in contact with the container 10. In another aspect, the diffuser acts as a one way check valve. In other aspects, the diffuser 28 functions to convert propellant from a liquid to a gas and to prevent the compound contained in the compound chamber 14 from coming into contact with the container 10. In yet another aspect, the diffuser functions to increase the temperature of the propellant.

An example of a diffuser 28 includes a frit, a plurality of frits, or a diffuser member or combinations thereof. In one aspect, the diffuser is a frit. In another aspect, the diffuser is a plurality of frits. In another aspect, the diffuser is a diffuser member.

In one aspect, the frit(s) are of any suitable size and shape and are formed using any suitable porous material of any suitable density. In one aspect, the frit is made of a hydrophobic material. In one aspect, the frit is made of an inert material to avoid chemically reacting with any of the compounds. The inert material may be metal or non metal. In one aspect, the frit is composed of metal. In another aspect, the frit is composed of a non-metal. In one aspect, the inert material is sintered nickel. As one example, a frit formed using a porous stainless steel having a pore size in the range of approximately 1 micron to approximately 100 microns can be used. In another aspect the pore sizes is in the range of about 1 to about 10, about 10 to about 20, about 20 to about 30, about 30 to about 40, about 40 to about 50, about 50 to about 60, about 60 to about 70, about 70 to about 80, about 80 to about 90, about 90 to about 100 microns, inclusive of endpoints. In another aspect, the frit can be formed using aluminum foam. The number and size of the pores and the overall dimensions (e.g., diameter and thickness) of the frit are set to maximize surface area for vaporization while limiting pressure drops accompanying passage of vaporized propellant through the frit. In certain aspects, the frit may be constructed of Teflon, glass, metal mesh, screen, porous metal, polyether ether ketone or another plastic material. In one aspect, the passage of liquid propellant through the increased surface area of the frit transitions the liquid to gas and increases the temperature of the resulting gas. In another aspect, the passage of gas propellant through the increased surface area of the frit increases the temperature of the gas.

As shown in FIG. 2, in one aspect, the diffuser 28 is disposed on the connection channel 22. In another aspect, the diffuser 28 is disposed within a drug chamber 24 whereby an intranasal dosage form is disposed in the drug chamber 24. A nozzle 26 is in communication with the drug chamber 24. The diffuser 28, drug chamber 24 and nozzle 26 are housed by a drug capsule 30 adjacent the actuator body 20.

The drug capsule body 30 may be of any suitable material to house the components. In one aspect, the drug capsule body 30 may be constructed from plastic. In one aspect, the drug capsule body 30 may taper at the distal end to allow the nozzle 26 to be brought closer to the septum. The taper functions to improve the positioning of the device at a suitable horizontal angle relative to the upper nasal cavity.

Figure 3:
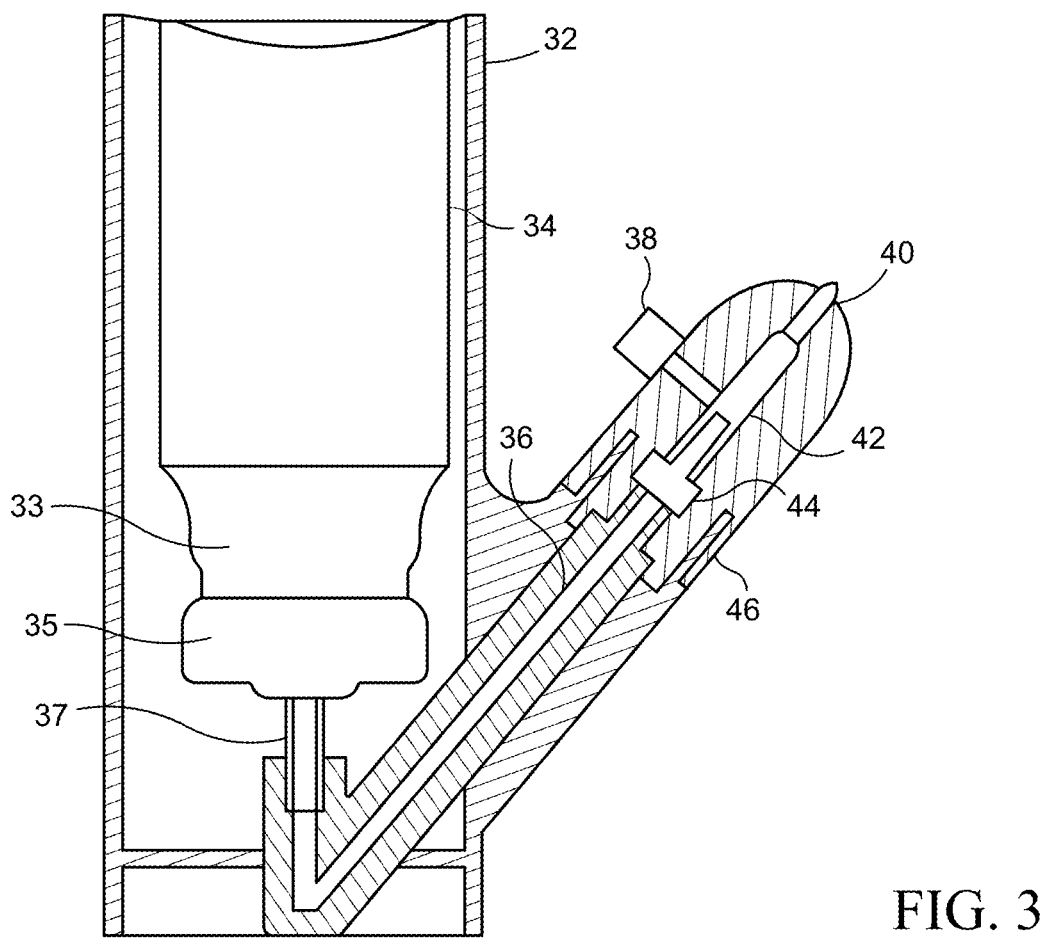
FIG. 3 shows an embodiment of the invention.

Shown in FIG. 3 is another embodiment of the device. The actuator body 32 (or, housing) houses the propellant canister 34 having a neck 33 and a metering valve assembly 35. A valve stem 37 is disposed within a connection channel 36. The propellant exiting the valve stem 37 is in a liquid form or a mixture of liquid and gaseous form. A diffuser 44 is disposed on the channel 36 and is adapted to convert a majority or all of the liquid propellant into gaseous propellant. The diffuser 44 is disposed within a drug chamber 42, whereby the intranasal dosage form is disposed in the drug chamber 42. A nozzle 40 is in communication with the drug chamber 42. The diffuser 44, drug chamber 42 and nozzle 40 are disposed within a drug capsule 46 adjacent the actuator body 32.

An insertion port 38 is provided for the insertion of a compound into the drug chamber 42. The insertion port 38 may be constructed from silicone or plastic. In one aspect, the needle of a syringe may be inserted through the insertion port 38 so as to inject the compound into the drug chamber 42. In one aspect, the compound is a drug. In another aspect, the compound is a diagnostic agent. In yet another aspect, the compound is not an imaging agent. The drug may be a liquid or a powder.

Figure 4:
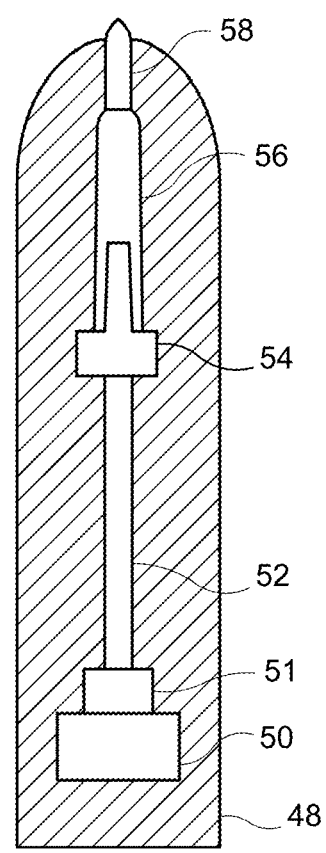
FIG. 4 shows another embodiment of the invention.

Shown in FIG. 4 is another embodiment of the device. A housing body 48 houses a pressurized propellant container 50, a connection channel 52, a release valve assembly 51, a diffuser 54, a drug chamber 56 and a nozzle 58. The pressurized propellant container 50 contains a liquid propellant and has a release valve assembly 51. A connection channel 52 is congruous with the release valve assembly 51 of the container 50 and a diffuser 54. The diffuser 54 is in communication with a drug chamber 56. In one aspect, the drug chamber contains a drug-containing intranasal dosage form. A nozzle 58 is in communication with the drug chamber 56.

Figure 5:
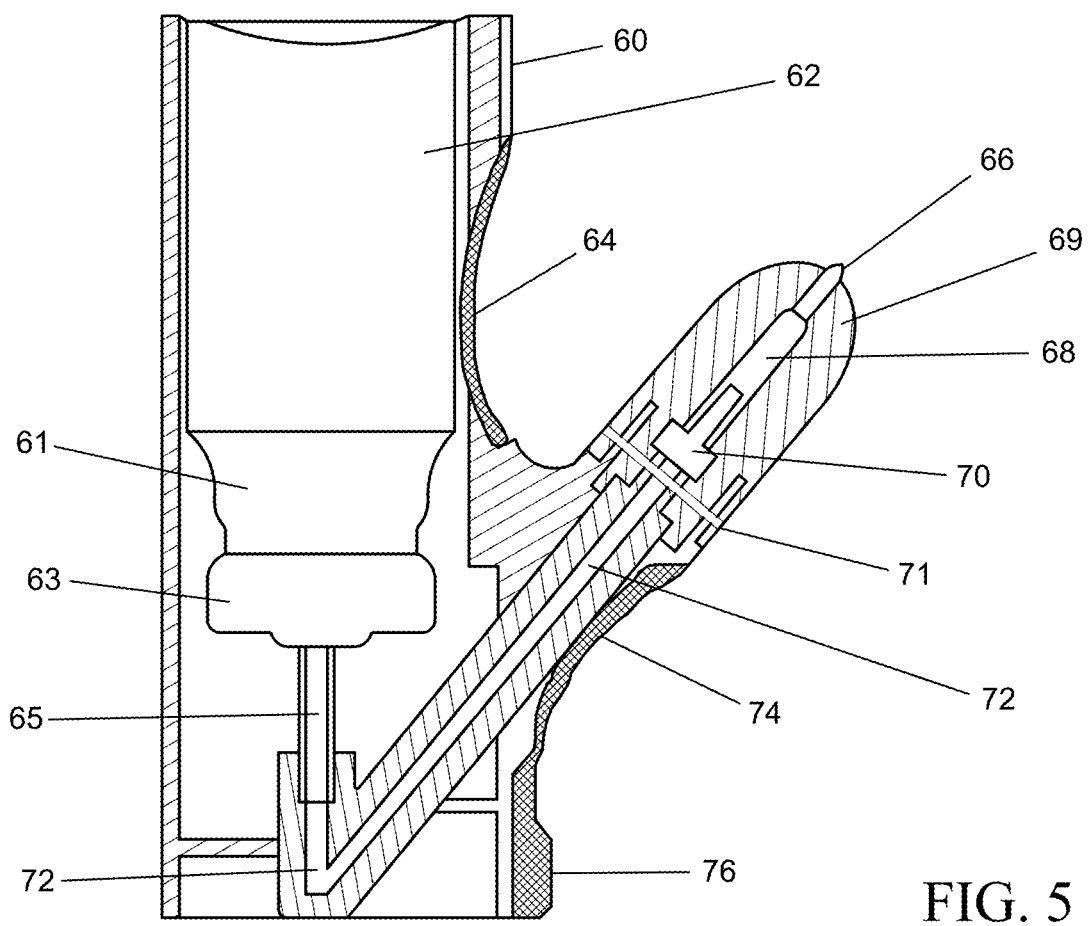
FIG. 5 shows another embodiment of the invention.

Shown in FIG. 5 is another embodiment of the device. An actuator body 60 houses a propellant container 62 having a neck 61, a metering valve assembly 63 and valve stem 65. A valve stem 65 is disposed within a connection channel 72. The propellant exiting the valve stem 65 is in a liquid form, gaseous form, or a mixture of liquid and gaseous form. A diffuser 70 is disposed on the channel 72 and is adapted to convert the liquid propellant into gaseous propellant. The diffuser 70 is in communication within a drug chamber 68. In one aspect, the drug chamber 68 contains an intranasal dosage form. A nozzle 66 is in communication with the drug chamber 68. The diffuser 70, drug chamber 68 and nozzle 66 are disposed within a drug capsule 69 adjacent to the actuator body 60. The actuator body 60 is shaped allowing or accommodating for an aiming guide. The aiming guide includes one, a plurality, or all of the nose-aiming guide 64, the septum-aiming guide 74, an upper lip aiming guide 76, and a visual indicator 71.

In one aspect, a nose-aiming guide 64 is provided on the actuator body 60. The nose-aiming guide 64 functions to accommodate the user's nose. In another aspect, the nose-aiming guide 64 functions to aim the nozzle 66 at the user's olfactory region.

In another aspect, a septum-aiming guide 74 is provided on the actuator body 60. In one aspect, the septum-aiming guide 74 functions to accommodate contacting the user's septum.

In yet another aspect, an upper lip aiming guide 76 is provided on the actuator body 60. The upper lip aiming guide 76 functions to accommodate contacting the user's upper lip. In one aspect, a visual indicator 71 is provided to alert the user to the length or amount of the capsule's 70 insertion into the user's nasal cavity. In one aspect, the visual indicator 71 is inserted to a specified amount or length into the user's nasal cavity.

Figure 6:
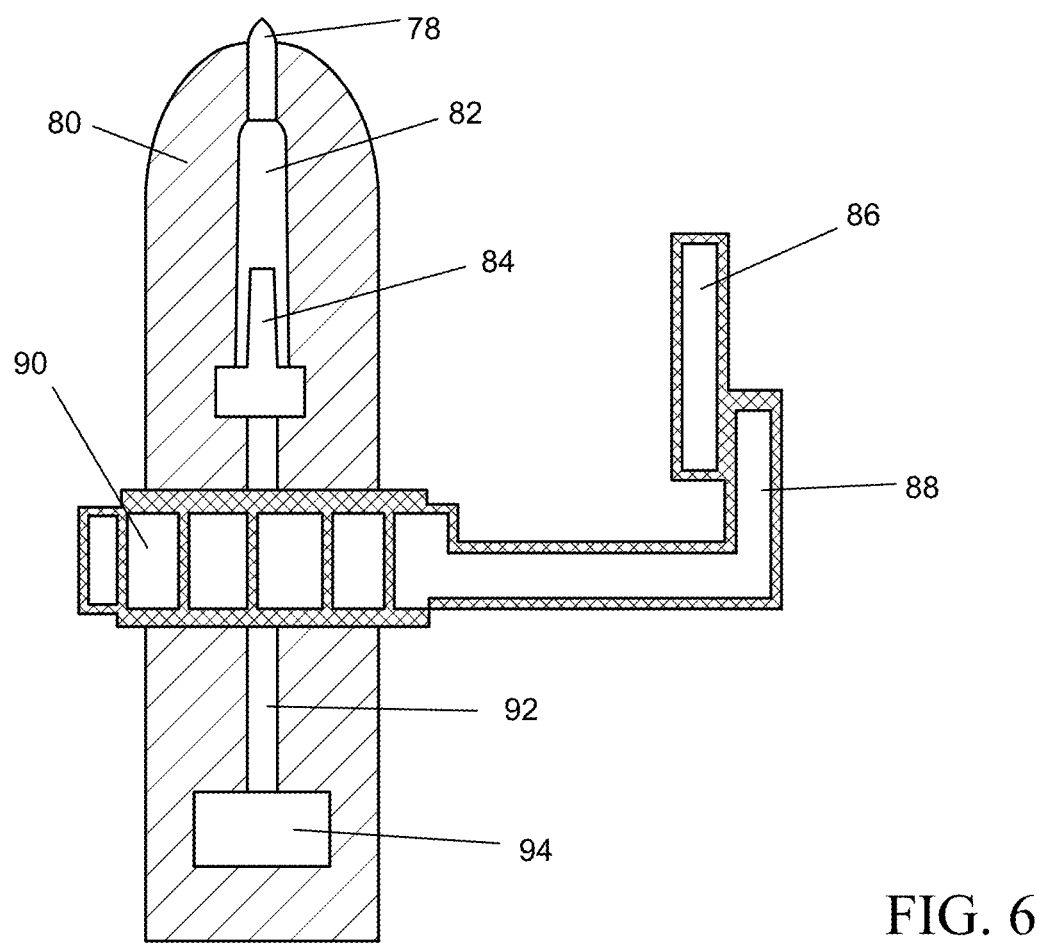
FIG. 6 shows another embodiment of the invention.

Shown in FIG. 6 is another embodiment of the device. A housing body 80 houses a pressurized propellant container 94, a release valve assembly, and a connection channel 92. The pressurized propellant container 94 contains the liquid propellant and has a release valve assembly. A connection channel 92 is in communication with the release valve assembly and a diffuser 84. The diffuser 84 is in communication with the drug chamber 82. In one aspect, the drug chamber 82 contains an intranasal dosage. A nozzle 78 is in communication with the drug chamber 82.

In one aspect, a guide function is provided. The guide function includes a guide post 86. The guide post 86 is adjacent to a guide post arm 88. The guide post arm 88 is integral to a rotation arm 90. The rotation arm 90 may be affixed or rotatably connected to the housing body 80 so as to accommodate right or left-handed users. The guide post 86 guides aiming of the nozzle 78 within the user's nasal cavity by entering the opposing naris of the user and by limiting the angle of administration. In one aspect, the guide post arm 88 and rotation arm 90 is constructed of plastic. In yet another aspect, the guide post arm and rotation arm is constructed of structural foam.

Figure 7:
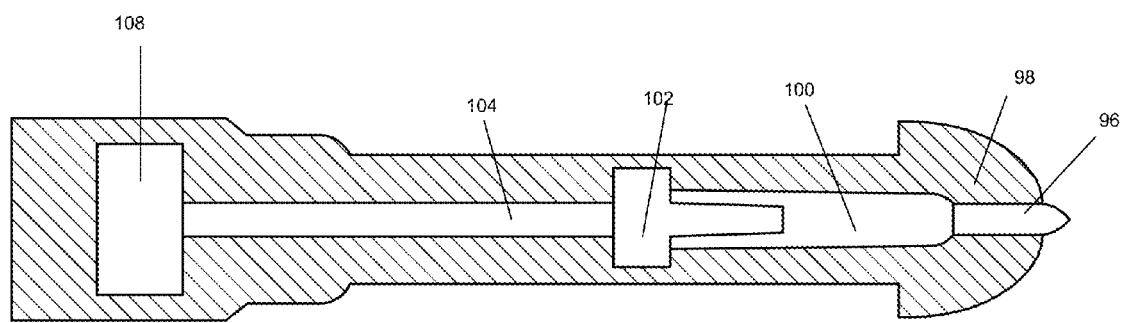
FIG. 7 shows another embodiment of the invention.

Shown in FIG. 7 is another embodiment of the device. A housing body 98 is provided to assist in placement and to house the various component structures shown. A pressurized propellant container 108 contains propellant and has a release valve assembly. A connection channel 104 is disposed between the release valve assembly and a diffuser 102. The diffuser 102 is disposed within a drug chamber 100, whereby the drug-containing intranasal dosage form is disposed within the chamber 100. A nozzle 96 is disposed on the chamber 100.

Figure 8:
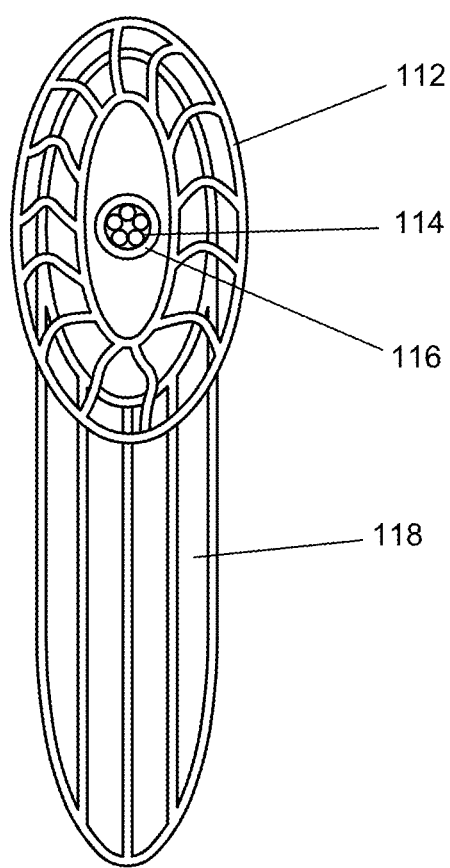
FIG. 8 shows another embodiment of the invention with a nasal guide attached.

Shown in FIG. 8 is a nasal guide 112 which could be added to the drug chamber 118. The guide would not obstruct the nozzle 116 or the nozzle orifices 114 and would serve to limit the placement/insertion of the device within the nasal cavity to the desired angle of administration.

Figure 9:
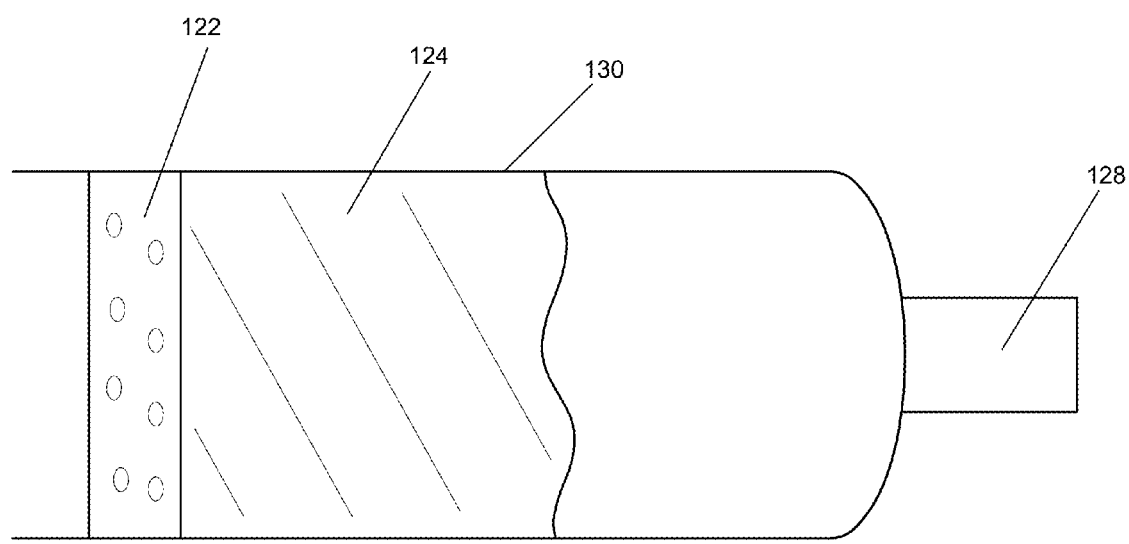
FIG. 9 shows an embodiment of a diffuser and compound chamber, whereby the diffuser is cylindrical and homogeneously porous.

FIG. 9 shows one embodiment of a diffuser 122 and its relationship with the drug chamber 130. Propellant comes into to contact with the diffuser 122. The diffuser 122 converts the liquid propellant to gaseous propellant. In one aspect, it converts a majority of the liquid propellant into a gaseous propellant. In another aspect, it converts a minority of the liquid propellant into a gaseous propellant. In yet another aspect, it converts all of the liquid propellant into a gaseous propellant. In one aspect, the diffuser 122 is cylindrical in shape. In yet another aspect, the diffuser 122 is congruous in shape with the compound chamber 130.

The diffuser 122 is porous. The pores may be homogenous in size and shape. In another aspect, the pores of the diffuser 122 are heterogeneous in size and shape. In yet a further aspect, the diffuser 122 is homogenously porous. In yet a further aspect, the diffuser 122 is heterogeneously porous. As shown in FIG. 9, the diffuser 122 is cylindrical in shape and is homogenously porous, whereby the gas may pass through the pores, but the pores are impervious to the drug product 124. The gaseous propellant then contacts a drug product 124 propelling the drug product 124 through a nozzle 128 and out of the device.

Figure 10:
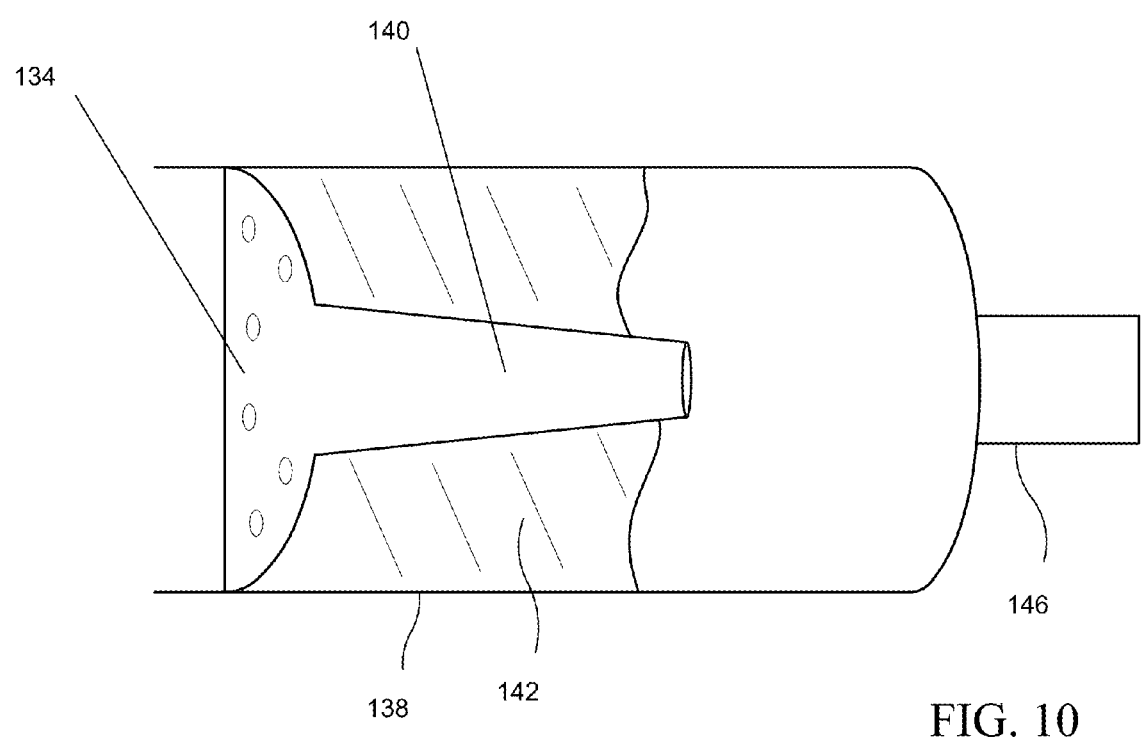
FIG. 10 shows an embodiment of a diffuser and compound chamber, whereby the diffuser is cylindrical and homogeneously porous with a non-porous open tipped cone extending into the drug product.

FIG. 10 shows is another embodiment of the diffuser 134 and its relationship with the drug chamber 138. A propellant comes into contact with the diffuser 134, propelling the drug product 142 through a nozzle 146. A portion of the gaseous propellant exiting the diffuser 134 is propelled through a diffuser extension 140, which aids in aerosolization of the drug product 142. As shown in FIG. 10, the diffuser 134 is heterogeneously porous via the diffuser extension 140.

Figure 11:
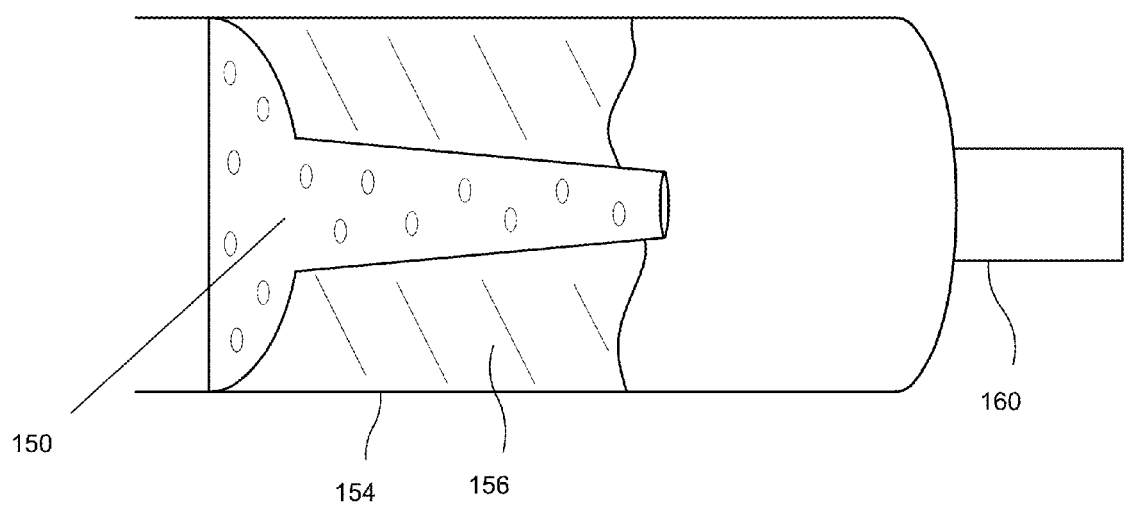
FIG. 11 shows an embodiment of a diffuser and compound chamber, whereby the diffuser is cylindrical with an open tipped cone extending into the drug product and is homogeneously porous.

FIG. 11 shows another embodiment of the diffuser 150 and its relationship with the drug chamber 154. Propellant comes into contact with the diffuser 150. The diffuser 150 is an extended shape or elongated shape. In one aspect, the diffuser 150 is an extended cylindrical shape. The function of the extended cylindrical shape is to increase the area of diffuser 150 in the drug chamber 154 and contact with any drug product 156 contained therein. A portion of the gaseous propellant contacts drug product 156 propelling the drug product 156 into a nozzle 160. Another portion of the gaseous propellant passes through the extended or elongated shape, aiding in aerosolization of the drug product 156. As shown in FIG. 11, the diffuser 150 is cylindrical in shape and is homogenously porous, whereby the gas may pass through the pores, but the pores are impervious to the drug product 156.

Figure 12:
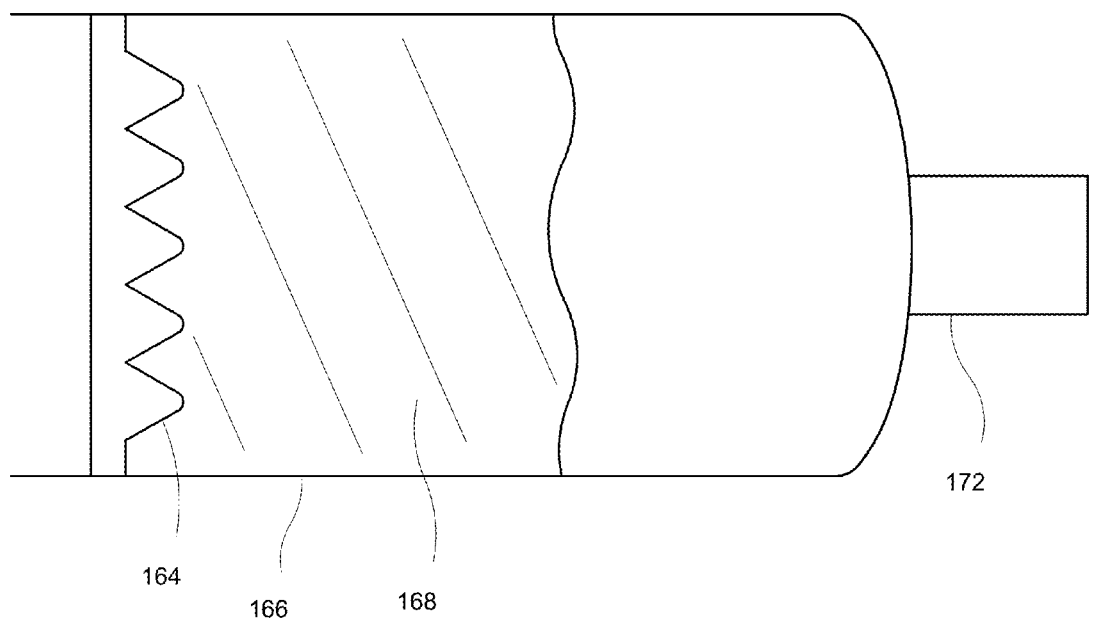
FIG. 12 shows an embodiment of a diffuser and compound chamber, whereby the diffuser is cylindrical with many open tipped cones extending from it which allow gaseous propellant to enter the compound chamber.

FIG. 12 shows another embodiment of the diffuser 164 and its relationship with the drug chamber 166. The propellant contacts the diffuser 164. The diffuser 164 has a plurality of conical points each with a distal hole at the tip, whereby the tips permit flow primarily of the gaseous propellant in the drug product 168. The propellant contacts the drug product 168 propelling it through the nozzle 172.

Figure 13:
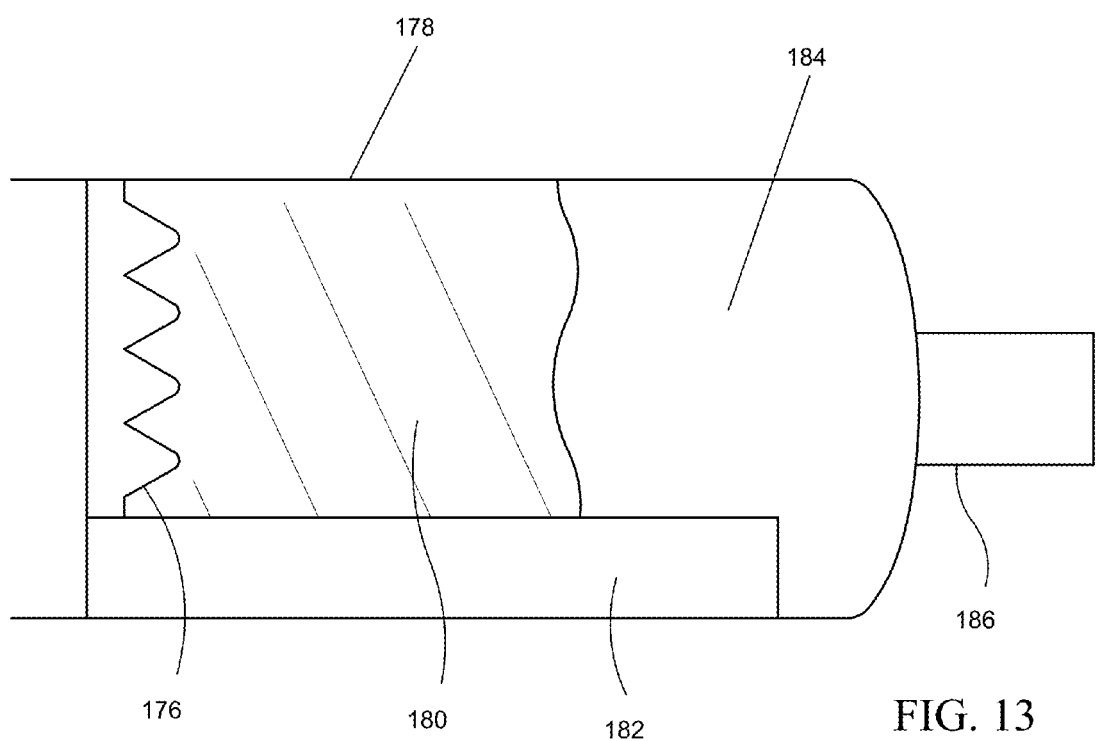
FIG. 13 shows an embodiment of a diffuser and compound chamber, whereby the diffuser is cylindrical with many cones extending from it which allow gaseous propellant to enter the drug chamber. It also includes a tube which allows propellant to enter the compound chamber ahead of the drug to assist in aerosolization.

FIG. 13 shows another embodiment of the diffuser and its relationship with the drug chamber 178. The propellant contacts the diffuser member 176. The diffuser member 176 has a plurality of conical points each with a distal hole at the tip, whereby the tips permit flow of the primarily gaseous propellant in the drug product 180. A diffusion tube 182 allows propellant mixture to bypass the drug product 180 into the void space 184. The gaseous propellant exiting the diffuser member 176 contacts the drug product 180 propelling it into the void space 184 and through a nozzle 186.

The diffusion tube 182 allows for respiration to occur concurrent with use of the device. As a user uses the device, the diffusion tube 182 allows for inhalation by the user to bypass inhalation of the drug product 180 contained in the drug chamber 178. Further, the diffusion tube 182 allows for propellant to aerosolize the drug product 180 as it comes into contact with the drug product 180 in the drug chamber 178. The drug product 180 exits the device aerosolized. In another aspect absent the diffusion tube 182, the drug product 180 exits the nozzle as a liquid or partial aerosol or a combination. In one aspect, a frit or a plurality of frits (not shown) is in communication with the diffusion tube 182 and/or diffusion member 176 so as to act as a check valve.

Figure 14:
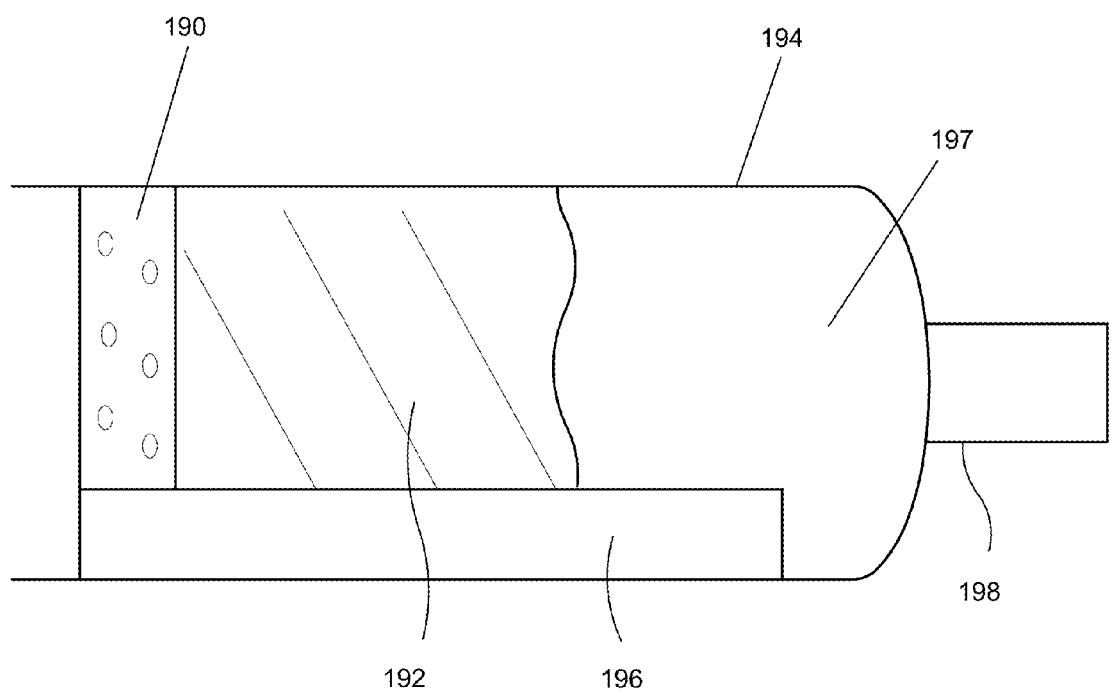
FIG. 14 shows an embodiment of a diffuser and compound chamber, whereby the diffuser is cylindrical and homogeneously porous. It also includes a tube which allows propellant to enter the compound chamber ahead of the drug to assist in aerosolization.

FIG. 14 shows another embodiment of the diffuser 190 and its relationship with the drug chamber 194. The propellant contacts the diffuser 190 that is homogenously porous whereby the gas may pass through the pores, but the pores are impervious to the drug product. A diffusion tube 196 allows propellant mixture to bypass the drug product 192 into the void space 197. The gaseous propellant exiting the diffuser 190 contacts the drug product drug 192 propelling it into the void space 197 and through a nozzle 198.

The diffusion tube 196 allows for respiration to occur concurrent with use of the device. As a user uses the device, the diffusion tube 196 allows for inhalation by the user to bypass inhalation of the drug product 192 contained in the drug chamber 194. Further, the diffusion tube 196 allows for propellant to aerosolize the drug product 192 as it comes into contact with the drug product 192 in the drug chamber 194. The drug product 192 exits the device aerosolized. In another aspect absent the diffusion tube 196, the drug product 192 exits the nozzle 198 as a liquid or partial aerosol or a combination. In one aspect, a frit or a plurality of frits (not shown) is in communication with the diffusion tube 196 so as to act as a check valve.

Figure 15:
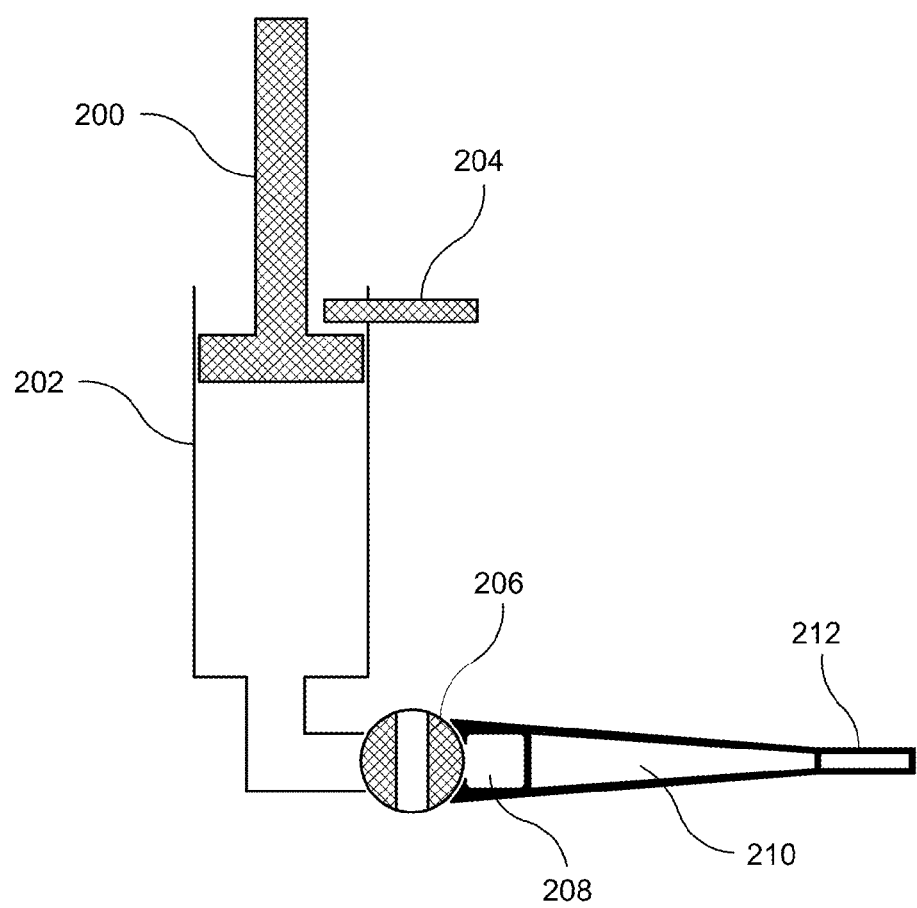
FIG. 15 shows an embodiment of the invention where the propellant is created by manual air compression.

FIG. 15 shows another embodiment of the device. The manual pressure actuator allows the user to administer the device without the need of a prefilled pressurized canister or HFA canister. This device has a piston 200 which is depressed into the air compression chamber 202 resulting in a quantity of compressed air held within the air compression chamber 202. The trapped air is thus raised from ambient pressure to several times that of ambient air pressure. In one aspect, the manual pressure actuator is a syringe or syrette. The device contains a lock pin 204 that is inserted to hold the piston in the high pressure position. In addition the device contains a trigger valve 206. In an aspect, the trigger valve 206 is similar to a stopcock valve. There is a diffuser 208 in communication with the trigger valve 206 and the compound holding chamber 210. The compound is placed in the compound holding chamber 210 which is in communication with a nozzle 212. While the device is put in the high pressure state, the trigger valve 206 is placed in the load position, which blocks the high pressure air in the air compression chamber 202. When the trigger valve 206 is moved into the open position by the user, the compressed air in the air compression chamber 202 travels through the diffuser and into the compound holding chamber where it mixes with the compound. A mixture of compressed air and compound then exits the device through the nozzle 212 with a positive velocity.

Figure 16:
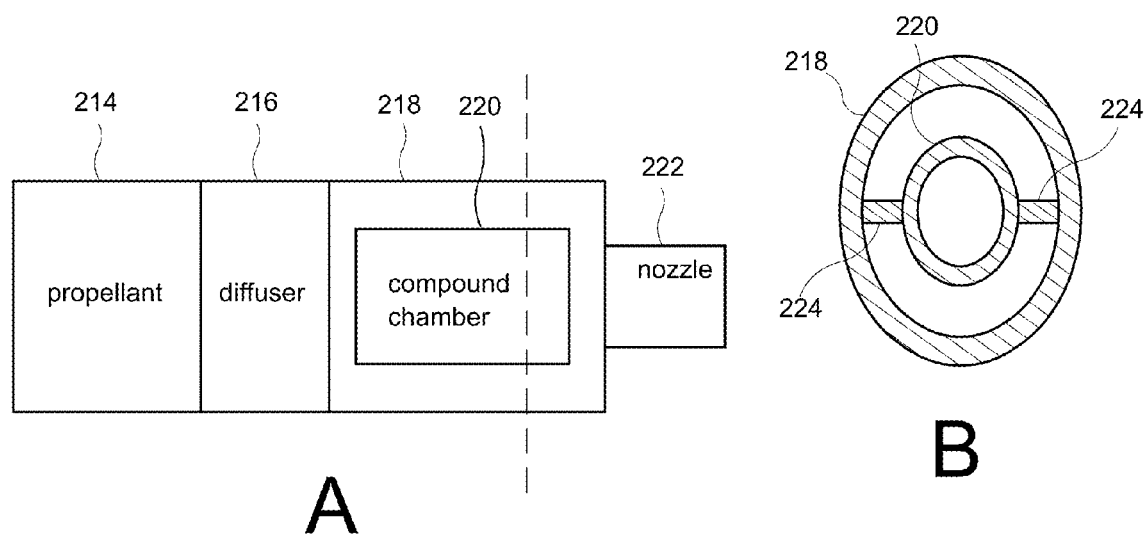
FIG. 16 A shows an embodiment of the device which has a compound chamber within the device body which allows for propellant flow through and around the compound chamber.

FIG. 16A shows another embodiment of the device which is suitable to deliver a compound into the nasal cavity of an animal or human. A pressurized propellant container 214 is in communication with a diffuser 216. The diffuser 216 is in communication with the interior of the housing body 218 and with the compound chamber 220. The interior of the housing body 218 is in communication with a nozzle 222. FIG. 16B is a cross section of FIG. 16A at the dashed line. FIG. 16B shows that the compound chamber 220 is connected to the housing body 218 by flanges 224. The propellant is diffused by the diffuser 216 and the flanges 224 allow the diffused propellant to travel both through the compound chamber 220 and also around the compound chamber 220. When the pressurized propellant container 214 is actuated to release an amount of propellant, the propellant travels through the diffuser 216. The diffuser disperses the propellant into the interior of the housing body 218 and into the compound chamber 220 where the propellant mixes with the compound. The propellant also travels on the outside of the compound chamber 220 and then mixes with the compound exiting the compound chamber 220. The mixture of pharmaceutical compound and propellant then exits the nozzle 222. As a user uses the device, the relationship of the compound chamber 220 with the housing 218 allows for inhalation by the user to bypass inhalation of the drug product contained in the compound chamber 220.

The device may be for pediatric or adult use. One of skill in the art can envision modifications of the device to accommodate for pediatric or adult use.

In another embodiment, the device delivers a compound through the mucosa or epithelium of the tongue, mouth, skin, or conjunctiva. In another embodiment, the method includes administering a composition of the compound on or to the tongue, on or to the skin, or on or to the conjunctiva of the subject.

In yet another embodiment, the device delivers the compound to the turbinate regions of the nasal cavity. In one aspect, the device delivers the compound primarily to the turbinate regions of the nasal cavity.

In additional embodiments, the device may be used for treatment, prevention, or palliative care. The device may be used in research or industrial purposes. The device can be used to disperse a compound which has been propelled by a propellant having been in communication with a diffuser. For example, the device may be used in agriculture to dispense an agricultural compound.

An intranasal formulation of an oxime is provided. Additionally, a method of intranasal administration of an oxime to the olfactory region is described.

Oximes can be delivered to the central nervous system (CNS) for the prevention, treatment, and palliative care of exposure to organophosphate (OP) compounds such as chemical warfare nerve agents (e.g. sarin, tabun, soman, Russian VX, etc.) or pesticides (e.g. diisopropylfluorophosphate). Oximes had traditionally been delivered, for example, intravenously. Intranasal administration of an oxime to the olfactory region allows for transport across the BBB.

Nerve agents containing organophosphorous compounds are a significant threat to the warfighter, who may be exposed in battlefield settings on land, sea, air and space. Civilian populations also face health risks associated with nerve agents during the use of commercially available pesticides, as do first responders to a terrorist attack. The current treatment regimen for nerve agent exposure includes the use of a cholinergic reactivator (pralidoxime, 2-PAM), muscarinic receptor antagonist (atropine) and an anticonvulsant (diazepam). While 2-PAM and atropine are available in multiple injection formats, (e.g. IV infusion or IM autoinjector), injection presents significant and practical challenges in the battlefields, such as the need to remove body armor, and have correct training in the use of autoinjectors. Moreover, newer oximes such as MMB4 and HI6 are difficult to formulate in current autoinjector formats. There is great need to develop practical, more effective and rapid onset systems capable of distributing anti nerve gas agents, such as oximes, capable of penetrating into the central nervous system (CNS) of subjects in battlefield and emergency situations.

The method for delivering an oxime across the blood brain barrier to a subject in need thereof includes administering to the subject a therapeutically effective dosage of an oxime, where the dosage is delivered to the upper olfactory region of the nasal cavity.

In one aspect of the method, the therapeutically effective amount of an oxime administered to the user is within the range of about 0.001 mg/kg to about 100 mg/kg.

In another aspect of the method, the therapeutically effective amount of an oxime administered to the user is within the range of about 0.01 mg/kg to about 10 mg/kg.

In yet another aspect of the method, the therapeutically effective amount of an oxime administered to the user is within the range of about 0.1 mg/kg to about 1 mg/kg. In one aspect, the mg/kg is mg of compound per kilogram of body weight. In another aspect, the dosage is a flat dosage independent of weight.

In performance of the method of delivery of an oxime intranasaly to the olfactory region includes providing the device described herein for insertion into the user's nasal cavity. The device is inserted into the user's nasal cavity. At least one therapeutically effective dose of an oxime is delivered via the device. At least one therapeutically effective dose of the oxime is delivered to the olfactory region. Delivery of the oxime to the olfactory region allows for delivery of the oxime across the BBB.

Oximes such as but not limited to 2-PAM (2-pyridine aldoxime methyl chloride), MMB4, HI6, TMB4, Hlo7 are currently used to treat OP exposure but they poorly penetrate the blood-brain-barrier. Thus, the oximes, in their current form of administration, do little to treat or prevent the CNS damage caused by these compounds.

By using the using the device described herein for the method, the compound, such as the oxime, can be self-administered, or administered by a battle-buddy or civilian, with or a user without prior medical training. The device delivers compound without requiring a specific breathing pattern by the user and can be administered to an unconscious user.

Direct transport percentage (DTP %) to the brain was calculated using an oxime to determine the amount of drug in the brain that was distributed directly from the nasal cavity to the CNS. In one embodiment, the DTP was 62.6+/−9.6%. In one aspect, the DTP was greater than 64.2%. In another aspect, the DTP was at least 64.3%. In another aspect, the DTP was at least 53%. In another aspect, the DTP was greater than 53%. In another aspect, the DTP was greater than 55%. In another aspect the DTP was at least about 55%, 60%, 65%, 70%, 75%, 80%, 85%, 90%, 95%, 99%, or 100%, inclusive of endpoints. In another aspect, the DTP was at least about 40%, 45%, 505, 55%, 60%, 65%, 70%, 75%, 80%, 85%, 90%, 95%, 99% or 100%, inclusive of endpoints.

The device deposits a compound on the olfactory region. In one embodiment, the percent deposition of the compound is at least 64.2%. In one aspect, the percent deposition of the compound was greater than 64.2%. In another aspect, the percent deposition of the compound was at least 64.3%. In another aspect, the percent deposition of the compound was greater than 50%. In another aspect, the percent deposition of the compound was greater than 55%. In another aspect the percent deposition of the compound was at least about 55%, 60%, 65%, 70%, 75%, 80%, 85%, 90%, 95%, 99%, or 100%, inclusive of endpoints. In another aspect, the percent deposition of the compound was at least about 40%, 45%, 505, 55%, 60%, 65%, 70%, 75%, 80%, 85%, 90%, 95%, 99% or 100%, inclusive of endpoints.

Compounds which can be delivered by the device described include but are not limited to those for the palliative, prevention or treatment of infectious diseases, inflammatory diseases, and oncology. Compounds which can be delivered by the device include but are not limited to those for the palliative, prevention or treatment of Parkinson's disease, Alzheimer's disease, depression, stroke, epilepsy, autism, lysosomal storage disorders, fragile X syndrome, ataxis, insulin deficiency, and blindness. Compounds which can be delivered include but are not limited to deferoxamine (DFO), glucagon-like peptide-1 antagonist, cephalexin, midazolam, morphine, insulin-like growth factor-1, nerve growth factor, insulin, oximes, imaging agents including but not limited to FDL and FLT, GDP-5, and cytokines including but not limited to interleukins (i.e., IL-1, IL-2, IL-3, IL-4, IL-5, IL-6, IL-7, IL-8, IL-9 and IL-10), interferons, and tumor necrosis factor (i.e., TNF-α and TNF-β).

The invention is further described in the following examples, which are in not intended to limit the scope of the invention.

EXAMPLES

Example 1

An oxime drug, 2-PAM, was administered into the olfactory nasal region in rats with the device, (e.g. a Pressurized Olfactory Delivery (POD) device). The brain and plasma concentrations of 2-PAM was measured at certain time points after drug administration. The device enabled delivery of 2-PAM resulted in higher brain exposure and lower plasma exposure compared to intravenous injection.

Animal use. Rats were used for deposition, tolerability and distribution experiments. Adult male Sprague-Dawley rats (200-300 g; Harlan, Indianapolis, Ind.) were housed under a 12 hour light/dark cycle with food and water provided ad libitum. Animals were cared for in accordance with institutional guidelines, and all experiments were performed with an approved protocol from the Pacific Northwest Diabetes Institute Institutional Animal Care and Use Committee under protocol number 12610.

Statistical analysis. In most cases where two values were compared a t-test was used. When more than two groups were compared, such as comparing the powder 2-PAM POD formulation with the aqueous 2-PAM POD formulation and the IV 2-PAM, a two-way ANOVA was used with a bonferroni post test. When comparing the AUC plasma and brain values which were derived from different animals at each time point the method described in Westin et al., 2006 was used. In all cases statistical significance was defined as $p<0.05$.

Aqueous formulations of 2-PAM were made by dissolving 2-PAM in deionized water. 2-PAM was dissolved into 500 µl of water at 10 mg/ml, 100 mg/ml, 250 mg/ml, and 500 mg/ml and left in a closed microcentrifuge tube at ambient temperature (25°). These water based formulations were then visually observed at 1 hour, 24 hours, and 48 hours for any cloudiness or precipitant.

Dry powder formulation of 2-PAM was prepared by placing the 2-PAM free drug in a microcentrifuge tube and grinding the drug with a motorized pestle (Kontes, Vineland, N.J.). The 2-PAM powder was then observed under a microscope to ensure the homogeneity of the powder formulation. The 2-PAM was ground with a pestle to ensure that there were no agglomerations of 2-PAM greater than 100 µm in diameter. Such larger agglomerates could clog the 810 µm diameter POD nozzle used in the rat experiments.

Figure 17:
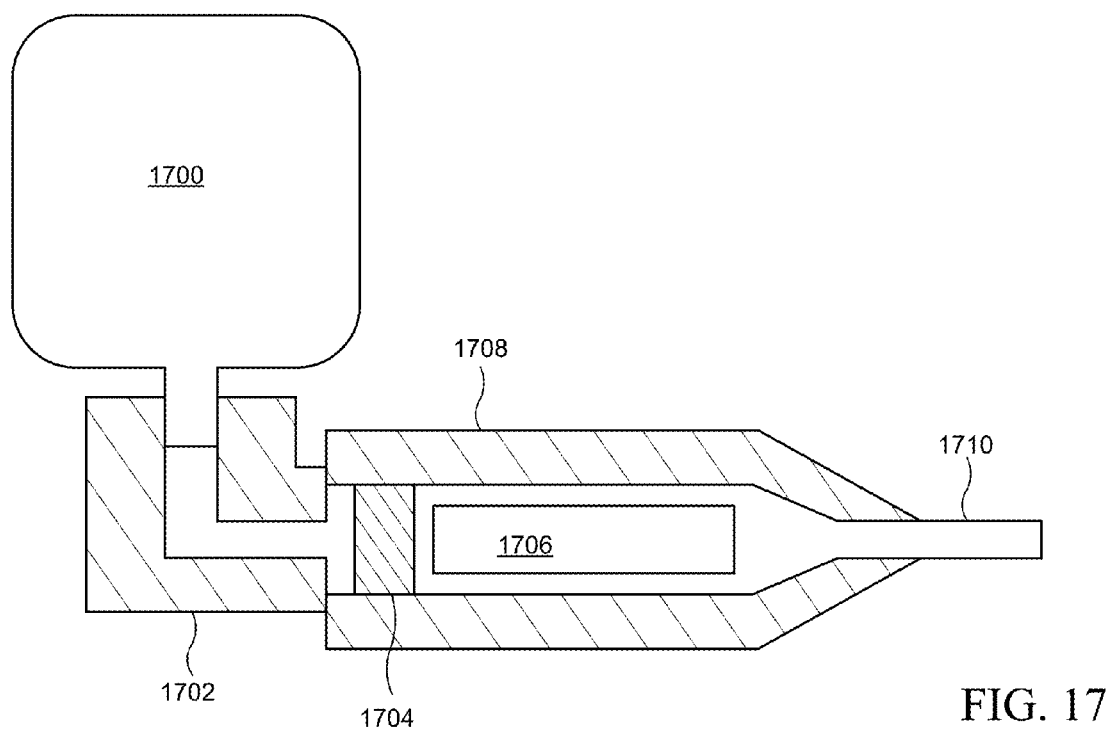
FIG. 17 shows a schematic drawing of the device used to administer 2-PAM drug to rats in Example 1.

The construction of the rat use POD nasal aerosol device is illustrated in FIG. 17. A meter dose inhaler (MDI) can dispensing 25 µl hydrofluoroalkane 227 1700 is attached to the plastic actuator 1702. The actuator is in gas communication with a polytetrafluoroethylene frit 1704 which had a 50 µm pore size. The frit 1704 is in communication with the dose holding cylinder 1706 which is placed inside the body 1708 of the POD in order to create an aerosolized flow. On actuation the HFA propellant 1700 is converted to a gas by passing through the frit material 1704 and then it mixes with the dose 1706 and the dose and propellant mixture exits from the 23 gauge stainless steel tubing nozzle 1710 which is covered with a fluorinated ethylene-propylene liner that was placed over the outside of the metal tip in order to protect the nasal epithelia from being damaged by the nozzle 1710 during use. The construction of the rat use POD device was successful and consistently delivered powder 2-PAM formulations with no measurable residual drug left in the device.

The basic operation of either POD device in rats was as follows. The animal was anesthetized with 5% isoflurane for 2 minutes to enable consistent administration. The rat was removed from the isoflurane chamber and placed in a supine position. The dose was loaded into the device and the nozzle was carefully placed 8.0 mm into the rat nasal cavity and pointed in the direction of the cribriform plate. Then the MDI can was pressed to discharge the dose into the rat nasal cavity. In addition, the dry powder dose chamber was weighed on a scale with a sensitivity of 0.1 mg (Mettler Toledo, Columbus, Ohio) before loading the dose, after the dose was placed in the dose loading chamber, and after firing to ensure that the correct dose was loaded into the device and that the complete dose was released into the rat nasal cavity.

Figure 18:
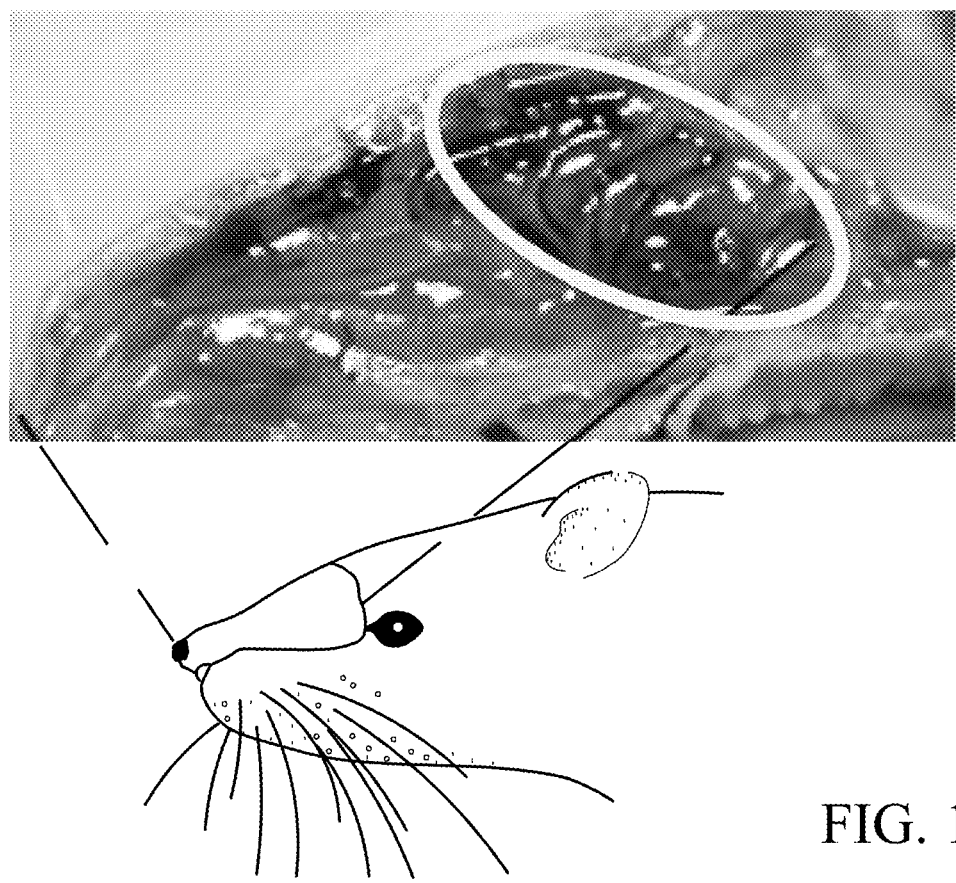
FIG. 18 demonstrates deposition testing of the POD device in the rat nasal cavity of 2-PAM (dark shading) being deposited on the olfactory region (light circle). Little drug was deposited on either the respiratory region of the nasal cavity and none was found in the trachea or esophagus.

The 2-PAM formulations were made with 0.1% coomassie blue dye in order to test nasal cavity deposition in rats. The animals were dosed using the dry power POD device as described above with a single dose of 2.5 mg dose of 2-PAM with coomassie blue. Shortly after administration was complete (<5 minutes), the animals were overdosed with 250 mg/kg pentobarbital. The nasal cavity was then bisected at the septum, the septum was removed, and the tissues were examined for dye localization. In addition the trachea and esophagus were dissected from the back of the mouth to the lungs to determine if the POD spray deposited any 2-PAM beyond the nasal cavity. This deposition study was performed with N=4 rats. The typical result of the deposition testing is shown in FIG. 18. In FIG. 18 the olfactory region of the rat nasal cavity in the upper panel is circled in white. The dark dye can be seen as being deposited primarily within this olfactory region.

A sensitive LC/MS method was established in order to determine the distribution of POD administered 2-PAM in both the plasma and the brain of rats. A fixed volume (20 µl) of 2Chlorolmethylpyridinium iodide d6 (Cerilliant, Palo Alto, Calif.) was added into each tissue and plasma sample to act as an internal standard. Tissue samples were homogenized in 3 mls of water. 60 µl of acetonitrile was added to the samples to cause protein precipitation. The samples were centrifuged for 10 minutes at 1000 g. An Agilent HPLC/MS series 1100 series B with autosampler (Agilent, Technologies, Inc., Santa Clara, Calif.) was used for quantification. The injection volume was 5 µl. The morphine samples were passed over a Phenomenex Synergi 4u PolarRP 80A (Agilent, Technologies, Inc., Santa Clara, Calif.) with a flow rate of 0.3 ml/min.

A standard curve was created on the day of analysis according to the same process described for the samples. Each standard curve was linear with a coefficient of linear regression R2>0.99. In addition, two quality control samples with a known amount of drug were processed on the day of analysis in order to ensure day to day consistency of the analytical assay.

This LC/MS method was successful and resulted in reproducible quantification of both tissue and brain samples. The 2-PAM detectable peaks were much higher than background in most cases. The sensitivity of this detection method was 0.05 µg/ml in plasma and 1.0 ng in brain tissue. This method could be used in future studies with primates or in clinical studies.

\In the tissue distribution experiments, the animals were anesthetized with 5% isoflurane for two minutes. Then the animals were removed from the isoflurane induction box and placed in a supine position. The animals were then dosed with either the POD device (2.5 mg in a single 10 µl dose) or via intravenous injection (2.5 mg in 500 µl). Animals that were sacrificed 5 minutes after dosing remained under 2% isoflurane anesthesia until they were sacrificed. The animals sacrificed at the remaining time points were allowed to wake up from isoflurane anesthesia and placed back into housing. At 3 minutes before the sacrifice time the animals were again exposed to 5% isoflurane and then quickly overdosed with Beuthanasia-D (Schering—Plough Animal Health Corp, North Chicago, Ill.). Using IV 2-PAM and the aqueous POD formulation of 2-PAM, animals were sacrificed at 5, 15, 30, 60, and 120 minutes (N=6). Animals dosed with the dry powder 2-PAM POD formulation were sacrificed at 5 and 15 minutes (N=6).

Immediately after death, the animal was decapitated. Blood was collected from the trunk and placed in a microcentrifuge tube with 10 µl of 40 mM EDTA. The plasma was separated from the blood by centrifuging at 6,000 g for 10 minutes. Then the plasma was frozen until it was analyzed for 2-PAM concentration with the LC/MS method previously described. The base of the skull and the parietal bones were quickly removed from the head. The brain was removed within 2 minutes of sacrifice. The brain was placed in a microcentrifuge tube and frozen until it was analyzed for 2-PAM concentration with LC/MS.

Figure 19:
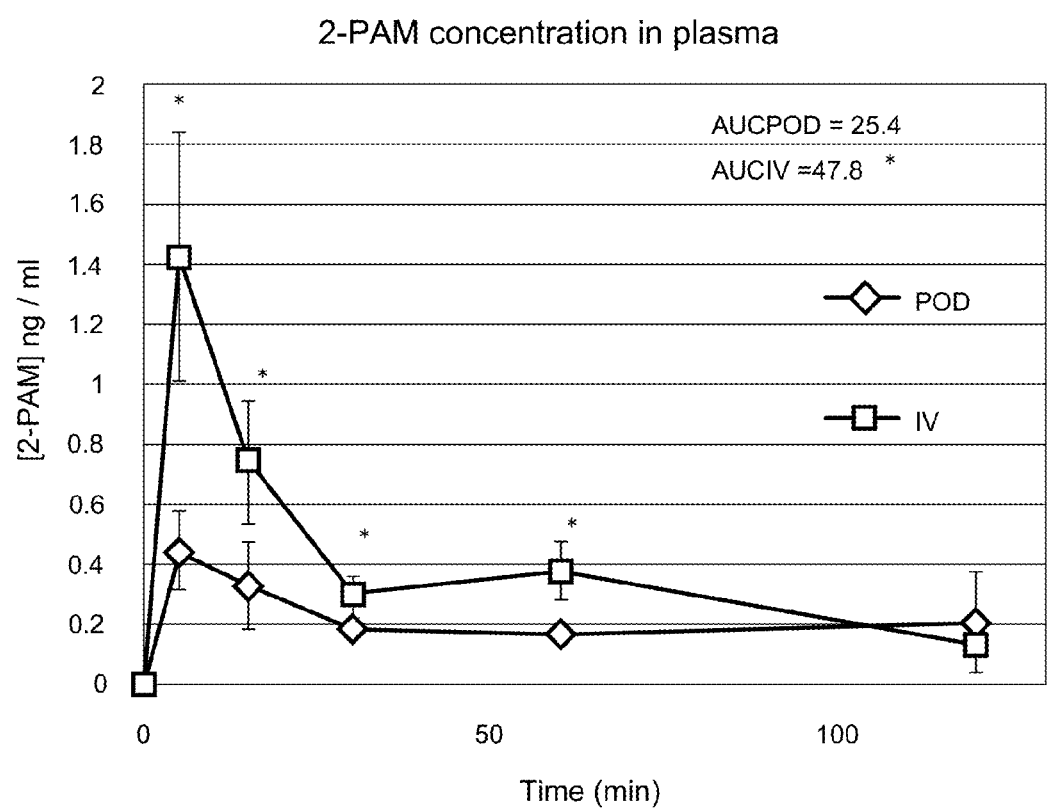
FIG. 19 is a graph demonstrating POD administration of a 2.5 mg dose of 2-PAM that resulted in significantly lower plasma values at every point in the first 60 minutes and overall lower plasma AUC. *=$p<0.05$

A direct transport percentage (DTP %) to the brain was calculated in order to determine the amount of drug in the brain that was distributed directly from the nasal cavity to the CNS. The DTP % is used to estimate the amount of drug in the brain that cannot be accounted for by systemic distribution. The DTP as defined was calculated as follows:

Administration of the aqueous formulation of 2-PAM with POD resulted in lower systemic exposure and greater CNS exposure compared to an equivalent IV dose. The IV dose resulted in a typical plasma curve with the highest point at 5 minutes (FIG. 19). The POD administered 2-PAM resulted in plasma concentrations that were lower than the IV values, which is not expected given 2-PAM's limited absorption across the nasal respiratory epithelium into the blood stream. The total plasma AUC was significantly lower after POD administration compared to IV $$\frac{AUC_{brain(IV)}}{AUC_{plasma(IV)}} = \frac{B_X}{AUC_{plasma(nasal)}}$$

$$DTP\% = \frac{AUC_{brain(nasal)} - B_X}{AUC_{brain(nasal)}} \times 100\%$$

administration.

Figure 20:
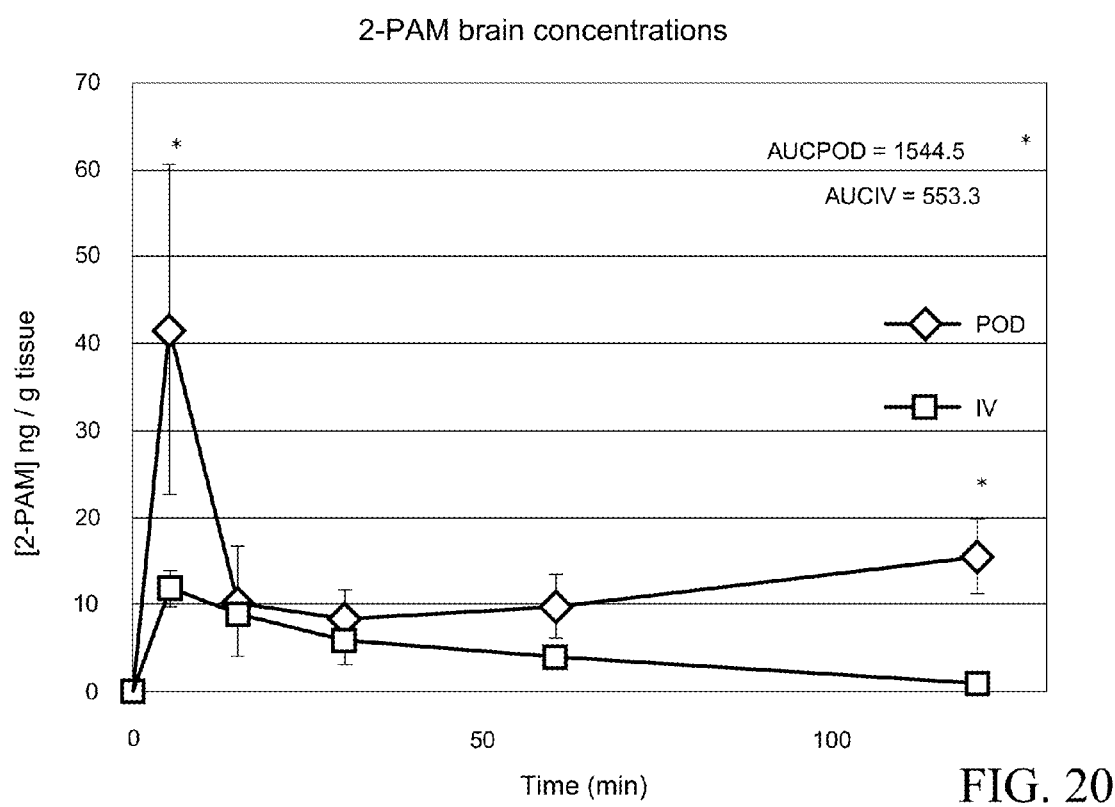
FIG. 20 is a graph demonstrating POD administration of a 2.5 mg dose of 2-PAM that resulted in significantly higher brain values at 5 and 120 minutes and an overall higher brain AUC. *=$p<0.05$
Figure 21:
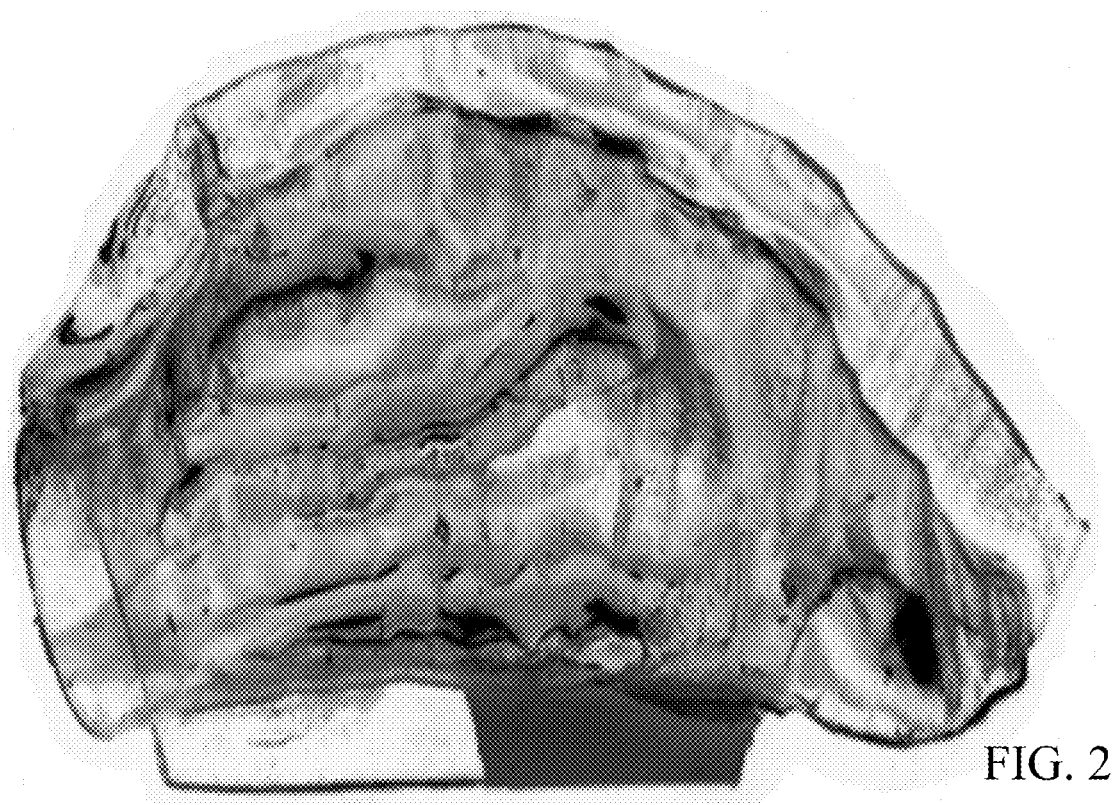
FIG. 21 shows the human nasal cavity model which was used in the deposition testing of the model drug fluorescein described in Example 3.
Figure 22:
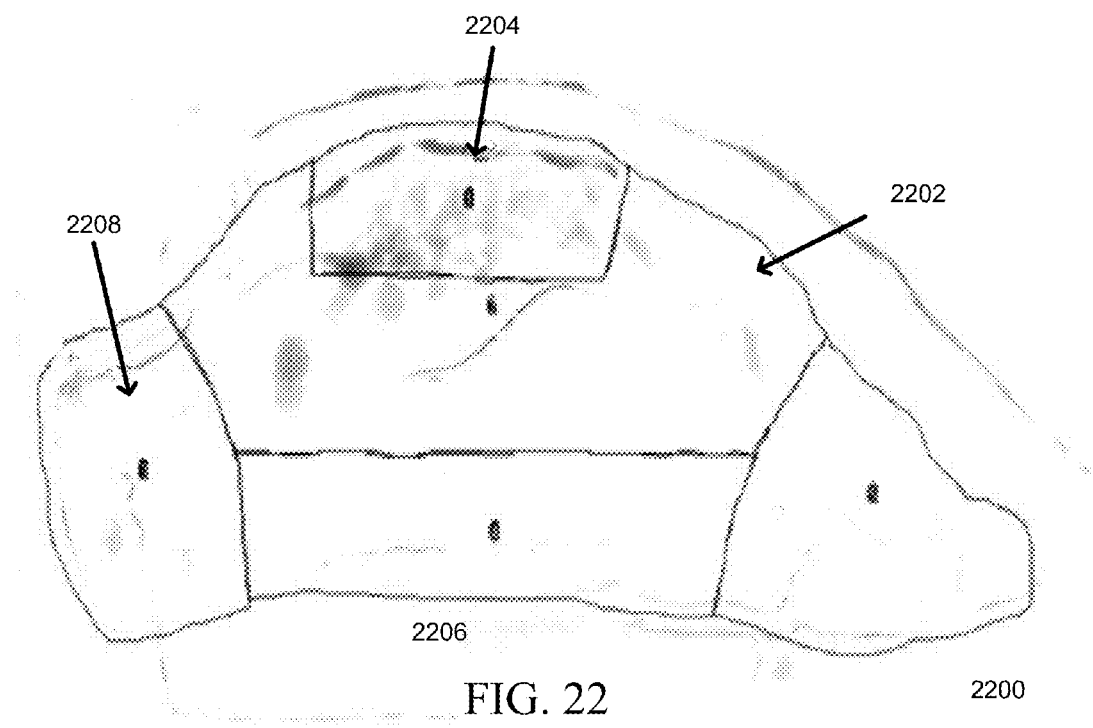
FIG. 22 shows a processed image of human nasal cavity deposition as described in Example 3. Five separate parts, vestibule 2200, turbinates 2202, olfactory 2204, base 2206, and esophagus 2208, were analyzed for deposition after a spray of the device.

In contrast to the plasma values, the brain concentrations of 2-PAM after POD administration were significantly higher than after IV administration at both 5 and 120 minutes (FIG. 20). In addition, the total brain concentration AUC was significantly greater after POD administration compared to IV. Of interest for the application of 2-PAM as a nerve gas exposure treatment is the fact that at 5 minutes after administration, POD 2-PAM resulted in 3.5× the brain concentration compared to IV administration.

The brain-to-plasma ratios were significantly higher after POD 2-PAM compared to IV at every time point except for 30 minutes (Table 1). These increased ratios point to the fact that a portion of the drug was directly delivered to the brain from the nasal cavity, effectively bypassing the blood brain barrier. When the direct transport percentage (% DTP) was calculated it was found to be 80.9%. This % DTP can primarily be accounted for by the large brain values found 5 minutes after POD 2-PAM administration. Table 2 shows brain to plasma concentration ratios. At each time point except for 30 minutes, POD administration resulted in significantly greater brain to plasma ratios with a 15.25 fold increased brain to plasma ration after 5 minutes.

| Time (min.) | POD | IV |
|---|---|---|
| 5 | 132.7* | 8.7 |
| 15 | 58.5* | 13.1 |
| 30 | 41.1 | 16.8 |
| 60 | 61.4* | 11.7 |
| 120 | 126.7* | 6.7 |

The powder formulation of 2-PAM administered via the POD device led to even greater 2-PAM concentrations in the brain (Table 2). The powder 2-PAM POD study was more limited than the aqueous formulation, but at 5 and 15 minutes after administration the powder formulation resulted in similar blood levels compared to the aqueous 2-PAM POD, but significantly higher brain concentrations.

TABLE 2

| time (min) | POD | IV | powder POD | | POD | IV | powder POD |
|---|---|---|---|---|---|---|---|
| | | | | | | standard deviation | |
| Plasma 2-PAM concentration (ng/g tissue) | | | | | | | |
| 5 | 0.44 | 1.42* | 0.46 | 5 | 0.1 | 0.4 | 0.27 |
| 15 | 0.33 | 0.73* | 0.38 | 15 | 0.1 | 0.2 | 0.11 |
| Brain 2-PAM concentration (ng/g tissue) | | | | | | | |
| 5 | 41.6 | 11.9 | 106.19* | 5 | 19.0 | 2.0 | 11.75 |
| 15 | 10.4 | 9.0 | 293.32 | 15 | 6.4 | 1.0 | 220.27 |

Table 2 shows distribution of the powder formulation of 2-PAM administered via POD. The powder formulation of POD resulted in plasma values at 5 and 15 minutes that were not significantly different than the liquid formulation of POD. However, the 2-PAM concentrations after POD administration of the powder formulation were significantly greater than either the aqueous POD 2-PAM or the IV 2-PAM. *=p<0.05

The pharmacokinetic and distribution experiments resulted in data supporting the potential of POD administered 2-PAM as a treatment for nerve gas exposure. The POD administration in both the aqueous formulation and the powder formulation resulted in high brain exposure within the first 5 minutes of administration.

Example 2

The device used in Example 2 is described in FIG. 3. The device in this example is referred to as a pressurized olfactory delivery (POD) device. In order to determine the amount of compound being delivered from the device to the olfactory region of the nasal cavity a method was developed for determining the percentage of dose deposited within key regions of a human nasal cavity model. This method relies on a quantitation by image analysis and is able to detect and quantitate deposition within 5 specified regions that describe the whole nasal model, including the upper olfactory region.

Materials: A human nasal cavity model was constructed from clear heat moldable plastic sheeting. (FIG. 21) This mold is thin-walled and is transparent to a blue light source that allows for the excitation of the indicator dye fluorescein used in the experimental doses. This human nasal cavity model was based on a computer model generated from MRI scans from multiple subjects (Liu, J Appl Physiol, 2009 March; 106(3):784-95). The model therefore represents an "average" human nasal cavity.

A stage for positioning the nasal models and aiming the POD device during targeting and actuation was designed and constructed. This stage was flexible enough in operation to allow for a wide set of aiming angles, both horizontal and vertical. By aiming the device at various angles with respect to the nasal cavity, the robustness of the device administration could be tested.

A thin walled transparent nasal model was prepared by coating the inside with a very thin layer of imitation mucus, which was simply a store bought hand sanitizer solution. The prepared model was then photographed in a custom made transilluminator/photo box as a blank reference for that particular experimental point. The model was then mounted onto the stage along with the POD device that has been loaded with a dose of 0.1 mg/mL Fluorescein/water. Immediately after POD actuation, the model was removed from the stage and held horizontally to prevent dose migrating. As soon as possible, the dosed model was placed in the transilluminator/photo box and photographed. The model was then washed under a stream of tap water and dried by shaking or forced air to be readied for another test. The two camera images were then digitally analyzed as described below to reveal deposition within the model.

Data processing of the blank and experimental images obtained was carried out with ImageJ software. For ImageJ to repeatedly compare images and perform background subtraction accurately, the digital photographs were taken with the model carefully held in the same register within the transilluminator/photo box. ImageJ performs three key functions: 1) the image was color processed with the RGB channel splitter. This function eliminates red and blue signals from the image, leaving primarily signal generated by the fluorescent signal from the fluorescein in the dose.

The ImageJ ROI manager allowed us to define five regions of interest; olfactory, turbinate, esophagus, base and vestibule which were quantitatively analyzed with each device administration. The regions are defined by the lines seen in FIG. 22 and these regions contain a specific area, in pixels that can be quantitated based on the signal intensity of the fluorescein. FIG. 22 also shows a typical spray pattern after a POD administration. The fluorescein administered into the model by the POD device can be seen as the dark intensity on the light background. It can be noted from in FIG. 22 that a majority of the administered dose resides within the olfactory region of the human nasal model. Each pixel within these photos can possess a value of 0 to 255. The Measure function of ImageJ calculates the mean pixel value over each defined region of interest. The total signal recorded within a particular region of interest is therefore the product of the mean pixel value by the number of pixels measured. Of additional interest is the reported Max value. Because the photo cannot record more than 256 levels of signal, we conclude that the assay is not valid if we receive values of 255 in that column, because we cannot be sure if the actual signal is not significantly greater than 255 if it could be measured. Such a situation would have the effect of underreporting signal in that ROI because the signal is effectively clipped. For this reason, the camera exposure settings are critical to ensure that the signals recorded fall within the sensitivity range of the method yet allow for the maximal sensitivity of the method as well.

In addition, our calculations involved the subtraction of values obtained from a blank recording. This is because there is some stray light leakage and always therefore the potential for background fluorescence involving the model and the imitation mucus. Because these elements are not perfect in application, we do a background photo record each time and do a subtraction for each data point. This method offers the advantage of providing fractional deposition on more than one region of the nasal model. It also offers clear qualitative photo/visual confirmation of the quantitative results.

The results of a deposition study are shown in Table 3. Two different POD devices were used and are referred to as Tip #1 and Tip #2. Each Tip was administered into the nasal model N=3 times at either 0 degrees horizontal angle with respect to the septum or 5 degrees horizontally towards the septum. All POD administrations were administered at a vertical angle of 55 degrees with respect to the base of the nasal cavity.

| | Tip #1 0 degrees | | Tip #1 5 degrees anterior | |
|---|---|---|---|---|
| Zone | Ave Distrib. | Std. Dev. | Ave Distrib. | Std. Dev. |
| Olfactory | 59.9 | 14.7 | 70.0 | 12.9 |
| Turbinate | 38.3 | 13.2 | 35.1 | 5.3 |
| Esophagus | −1.4 | 4.7 | −3.1 | 12.1 |
| Base | 3.6 | 4.1 | 0.7 | 2.5 |
| Vestibule | −0.4 | 4.6 | −2.7 | 2.8 |

| | Tip #2 0 degrees | | Tip #2 5 degrees anterior | |
|---|---|---|---|---|
| Zone | Ave Distrib. | Std. Dev. | Ave Distrib. | Std. Dev. |
| Olfactory | 58.2 | 3.9 | 61.1 | 7.3 |
| Turbinate | 49.1 | 12.1 | 38.5 | 3.6 |
| Esophagus | −4.6 | 5.2 | −0.1 | 4.6 |
| Base | −0.8 | 1.5 | 0.8 | 0.1 |
| Vestibule | −1.9 | 3.4 | −0.4 | 2.3 |

Example 3

Figure 23:
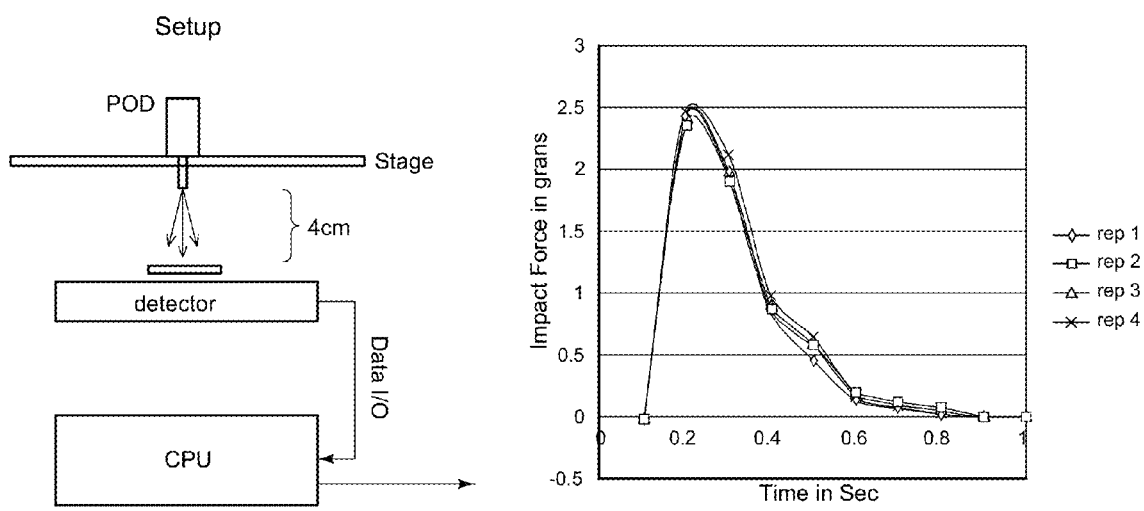
FIG. 23 is a schematic showing the experimental setup for the impaction testing described in Example 4.

Impaction force testing was used to compare several nozzle/dose chamber configurations with MDI drivers to several commercial nasal spray products. Impact impaction force is an ideal method to characterize plume characteristics that are important for dose delivery consistency, dose localization and dosing comfort and safety. A schematic of the experimental setup used in this example is shown in FIG. 23.

Impaction force measurements were carried out on a Mettler Toledo XS 64 with data output set at 10 per second coupled to an Apple MacBook Pro 2.2 GHz Intel Core 2 Duo processor, 4 GB 667 MHz DDR2 SDRAM via a ft. RS232 (Mettler Toledo) to USB cable (Gigaware) with supporting driver software. Data acquisition was carried out using Windmill Logger version 4.07, release 7 (Windmill Software Ltd.) in a Windows Vista virtual machine environment using Parallels Desktop 5 for Mac on the MacBook Pro. Data collected via Windmill Logger was imported directly into Microsoft Excel for graphical processing and analysis.

An impaction force stage was constructed to perform the measurements. This stage included means for accurate level and distance controls along with customized holders for the individual devices tested. Actuation was carried out manually. POD or commercial devices were aligned to impact the direct center of a 16.9 gram aluminum pan, 74 mm×80 mm. The pan was cleaned of dose/debris between each data shot. The distance from nozzle aperture to pan was 4 cm, consistent with the conclusions of Guo, et al. 2009 (Guo, J Pharm Sci., 2009, August; 98(8):2799-806.) as being within the 3 cm to 6 cm window of distances that generate the highest impaction forces and also consistent with our target distances in human nasal models. MDI triggered values obtained via valve actuation as tested was broadly insensitive from shot to shot when used as directed. The only effects seen were lower values if actuated very slowly.

Three commercial nasal spray products were tested in this Example: Rite Aid Pump Mist Nasal relief, oxymetasoline HCL 0.05%; NeilMed NasoGel For Dry Noses, Saline gel spray; and Rite Aid NoDrip Nasal Spray, pump, oxymetazoline, 0.05%.

The device used in this study is shown in FIG. 3 and is referred to as a pressurized olfactory delivery (POD) device in this Example. The POD nozzle was compared to the commercial spray pumps tested above. In this Example we tested the POD device under the same parameters as the commercial sprays using MDI canisters loaded with a 5% Ethanol, fluorescein mixed with either HFA 134a or HFA 227. The MDI valves were set to deliver a fixed volume of 50 uL.

The impaction forces measured for three commercial pump style nasal sprays were found to generate peak forces generally below 0.8 grams. These products are noted for either generating very broad spray patterns or slow moving streams of gelatinous material. The forces generated from these tested products fall well below the forces quoted by Guo et al., 2009 of 3.0 to 4.9 grams. The POD device generated impaction force measurements with peaks near 4 grams with an average of just below 3 grams of force when the more highly volatile HFA 134a was used. This force dropped to below 2 grams when HFA 227 was used instead. In either case, the impaction forces for the POD device also fell well within the range of impaction forces measured for commercial MDI device by Guo et al., 2009, which showed a maximum value of 6.5 grams.

It was found that the impaction forces measured are affected by the HFA type used and the volume of HFA dispensed by the MDI canister. Also the dose chamber and nozzle configuration have impacts on impaction forces. In no case have we measured forces greater than that measured for the one commercial product referenced in the Guo et al. paper.

Example 4

In this example the device, referred to as a pressurized olfactory delivery (POD) device, was tested to determine if the device would release a cold temperature spray. This testing involved the measurement of surface temperature changes on the target region caused by HFA POD. A schematic of the experimental setup used in this example is shown in FIG. 24.

The hydrofluoroalkane (HFA) used as a propellant in the POD device is released from the metering can as a liquid. Very quickly after release the HFA vaporizes and expands to form the pressure impulse that drives the dose through the POD nozzle. It is also a characteristic of the HFA POD that the HFA gas is expelled toward the target 2400 along with and after the dose is delivered. The expansion of the HFA causes a marked drop in temperature of the propellant gas during the firing process. In order to establish whether this temperature drop is transferred to target tissues and to what extent, we designed and performed experiments to detect and measure the surface temperature of targets during and immediately after they were impacted by the device while only releasing HFA or while releasing a mixture of HFA and liquid compound (as it would be used for administering a liquid drug product).

Materials: Kintrex infrared thermometer 2402, model IRT0421, capable of measuring surface temperature without actually contacting the surface being tested. Temperatures are reported in degrees Fahrenheit. An actuator fitted with a HFA 134a canister designed to deliver 50 µL of propellant, Kimwipe paper wipes, petri dish 2404, 1% agarose/water 3 tips, including a high impedance, low impedance nozzle and open configuration/absent frit.

Figure 24:
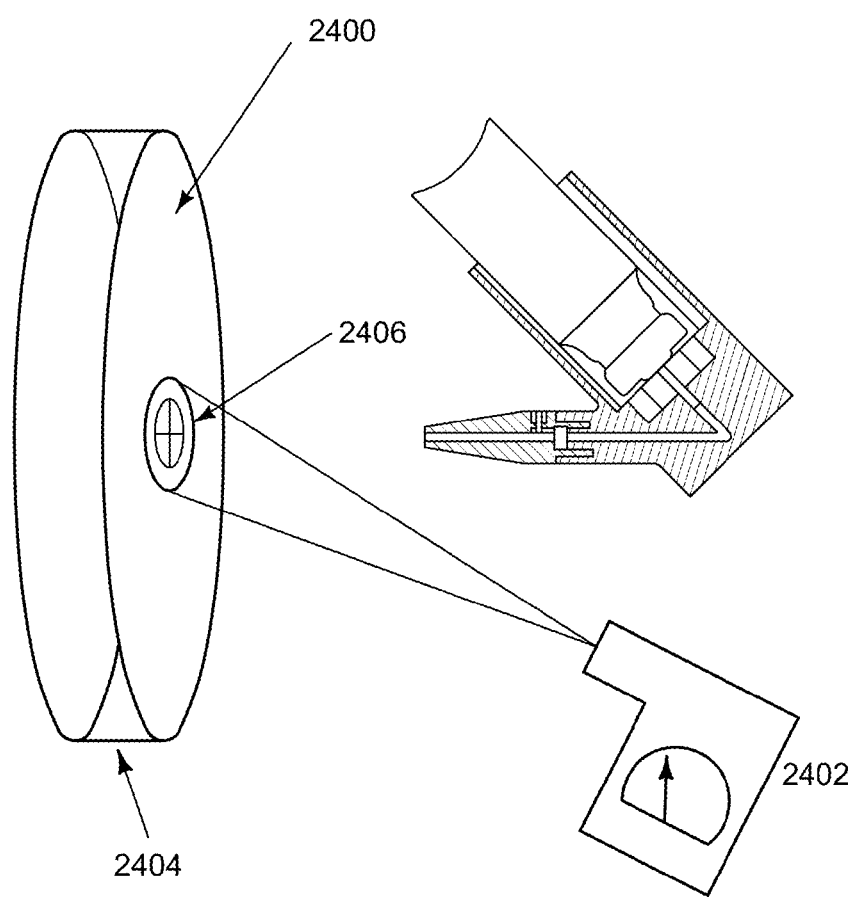
FIG. 24 is a schematic of the experimental setup for estimating any temperature changes on a surface that the device is targeting, which is described in Example 5. A laser thermometer was used to measure the surface temperature of a target. The device sprayed either only HFA gas or HFA gas mixed with a liquid dose and any temperature fluctuations were noted.

FIG. 24 illustrates the experimental setup for measuring temperature changes during the firing of the POD device under different conditions. The thermometer 2402 was positioned 4 cm from the target 2400. At that distance the thermometer 2402 "sees" and reads from a circular spot of 0.33 cm diameter 2406 (target circle in FIG. 24).

Three tip configurations were tested. 1. A tip with a high impedance nozzle fitted. A high impedance nozzle is sufficiently restrictive to flow of HFA gas that the nozzle is the limiting feature of the POD system. It releases gas over a longer duration. 2. A tip with a low impedance nozzle fitted. In this tip, the frit, near the actuator end of the tip is actually the limiting feature of the device. It releases gas faster than the high impedance nozzle. 3. A tip that contains neither a nozzle nor frit. This tip offers essentially no restriction to HFA gas or liquid flow through the device. With these three configurations, we expected to understand how restrictions on gas flow affects the temperature of target 2400 upon firing and also define the distinct role that the teflon frit plays in diffusing and facilitating the transition of HFA from the liquid state to the gaseous state.

We also tested the effect of target proximity to the nozzle with respect to temperature changes experienced by the target 2400. We fired from a distance of 4 cm and 2 cm.

In addition, we fired the device at three different targets. 1) We used a very low mass target 2400. This target 2400 was constructed of a Kimwipe tissue paper. We anticipated that a low mass target would have a very low thermal inertia and therefore would display much more change in temperature upon firing. 2) We created a mock epithelium (epithelium mimic #1) by overlaying a Kimwipe tissue paper wipe onto 1% agarose/water. This was designed so that the thermometer 2402 would react to a similar color and texture surface as the low mass target. 3) Another mock epithelium (epithelium mimic #2) made from 1% agarose/water with Kimwipe paper embedded just below the surface (less than 0.5 mm) of the agarose. This target 2400 was designed in case the thermometer 2402 would react to the paper layer just below the essentially clear agarose to see if the temperature effects were mostly superficial.

In addition, some temperature measurements were done on the epithelium mimics when a 50μL water dose was added to the setup. Table 4 summarizes the temperature changes detected upon the firing of only hydrofluoroalkane propellant. The temperature change in degrees Fahrenheit is represented by the symbol Δ. We believed and confirmed that this would create the conditions for the most dramatic temperature changes. With the low mass, low thermal inertia paper target, the greatest temperature change was when no frit or nozzle was installed in the tip. The data for this condition was closely clustered near −25° F. Indeed, with this setup particulate or mist can be seen ejecting from the end of the tip, suggesting that a certain fraction of the HFA remains liquid through its transit through the actuator body and tip. Any liquid HFA that were to reach the target 2400 would then ablate on the target and could explain the dramatic temperature drops seen.

In addition, some temperature measurements were done on the epithelium mimics when a 50 μL water dose was added to the setup. Table 4 summarizes the temperature changes detected upon the firing of only hydrofluoroalkane propellant. The temperature change in degrees Fahrenheit is represented by the symbol A. We believed and confirmed that this would create the conditions for the most dramatic temperature changes. With the low mass, low thermal inertia paper target, the greatest temperature change was when no frit or nozzle was installed in the tip. The data for this condition was closely clustered near −25° F. Indeed, with this setup particulate or mist can be seen ejecting from the end of the tip, suggesting that a certain fraction of the HFA remains liquid through its transit through the actuator body and tip. Any liquid HFA that were to reach the target would then ablate on the target and could explain the dramatic temperature drops seen.

TABLE 4

| | Low Impedance Nozzle | | | | | |
| --- | --- | --- | --- | --- | --- | --- |
| | 4 cm target | | 2 cm target | | No Frit/Nozzle | |
| | −Δ | −ΔMax | −Δ | −ΔMax | −Δ | −ΔMax |
| Low Mass | 2.5 | 3.7 | 4.4 | 5.6 | 25.2 | 27.2 |
| epithelium mimic #1 | 0.5 | 1.1 | 1.1 | 1.9 | 3.9 | 4.4 |
| epithelium mimic #2 | 1.0 | 1.5 | 0.9 | 1.8 | 4.2 | 5.3 |
| | High Impedance Nozzle | | | | | |
| | 4 cm target | | 2 cm target | | No Frit/Nozzle | |
| | −Δ | −ΔMax | −Δ | −ΔMax | −Δ | −ΔMax |
| Low Mass | 1.9 | 3.2 | 2.9 | 5.2 | 25.2 | 27.2 |
| epithelium mimic #1 | 1.2 | 3.5 | 1.2 | 1.6 | 3.9 | 4.4 |
| epithelium mimic #2 | 1.7 | 2.6 | 2.5 | 3.2 | 4.2 | 5.3 |

In contrast, all other experimental conditions resulted in far smaller temperature drops at the target. Modest drops of 3-4° F. were seen with the unobstructed tip on the epithelium mimics. It is clear the thermal capacity of the target is critical in this analysis.

Inclusion of the Teflon frit and nozzle into the tip resulted in even smaller temperature drops. Against the low mass tissue target, the low impedance nozzle resulted in the greatest temperature drop, with a maximum value of 5.6° F. at a distance of 2 cm. The high impedance nozzle resulted in slightly lower temperature drops. Typical values were 3° F. or less.

There is a slight trend depending on tip distance to target. As would be expected, shots at closer range can result in lower temperatures at the target.

When a dose load of 50 μL water was added to the tip that included a Teflon frit and low impedance nozzle very small temperature effects were seen. The data ranged from a 0.5° F. drop to a 0.2° F. increase. It was determined that with the small changes seen and the difficulty of handling the liquid doses in the experimental setup that we would not be able to get reliable data with liquid doses. However we believe the data collected with the liquid doses in consistent with predicted outcomes.

The hydrofluoroalkane propellant used in the POD device will have very minimal effects on the temperature of impacted tissues. The data show the Teflon frit's function in the POD and the decrease in the temperature of the impacted site when only HFA is delivered. In addition, a typical load of 50 μL will itself likely reduce any temperature effects.

Example 5

In assaying the targeting of the human olfactory region with a drug product, 2 formulations of 2-PAM were delivered from the device into a human nasal cavity model and analyzed for olfactory deposition.

A silicon rubber human nasal cavity model was purchased from Koken Inc. (Tokyo, Japan). A trace amount (0.1%) of Coomassie blue (SigmaAldrich, St. Louis, Mo.) was mixed into the dry powder 2-PAM. The dry powder 2-PAM and Coomassie blue were crushed to a homogenous powder with a mortar and pestle. 0.1% rhodamine B was added into the aqueous formulation (250 mg/ml) for visualization within the nasal cavity model. The dry powder formulation was sprayed into the model nasal cavity (N=10) with the device and pictures were taken to get a qualitative measure of deposition in the olfactory region. The pictures were judged as to whether a majority of the powder 2-PAM was deposited in the olfactory region.

The same was done with the aqueous formulation, and the deposition in the olfactory region was also quantified by weight for this formulation (N=10). The olfactory region of the nasal cavity model was cut from the model so that it was removable. The olfactory region was weighed before the POD spray and after the spray and the percent of dose administered to the olfactory region was calculated by weight.

The dry powder 2-PAM formulation administered into the human nasal cavity was effective in depositing of drug in the olfactory region. Qualitative examination of 10 administration attempts into the model consistently was judged to show a majority of drug (about 50% or greater) in the olfactory region. In addition to depositing drug on the olfactory region, the dry powder POD device deposited a substantial amount of the 2-PAM dose at the interface with the cribriform plate area of the model which separates the olfactory region of the nasal cavity from the brain.

The aqueous 2-PAM formulation displayed similar patterns of deposition in the human nasal cavity model as the dry powder formulation. In addition to the qualitative photos of the human nasal cavity, 62.6±9.6% of the dose was determined to deposit in the olfactory region of the nasal cavity.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We Claim:

1. A device for delivering a compound to an olfactory region of a nasal cavity, the device comprising:
   a canister capable of containing a propellant,
   a porous frit in communication with the canister, the porous frit being a disk-shaped member including at least one conical shaped member having a distal aperture,
   a compound chamber in communication with the porous frit, the compound chamber configured to hold the compound, and
   a nozzle in communication with the compound chamber, wherein the device is configured to deliver the compound to the olfactory region of the nasal cavity.

2. The device of claim 1, wherein the canister is pressurized.

3. The device of claim 1, wherein the propellant is at least one of a hydrofluoroalkane, nitrogen, or a chlorofluorocarbon.

4. The device of claim 1, wherein the compound is a drug or a diagnostic agent.

5. The device of claim 4, wherein the drug is an oxime.

6. The device of claim 4, wherein the diagnostic agent is an imaging agent.

7. The device of claim 6, wherein the imaging agent is fluorodeoxyglucose or fluorothymidine.

8. The device of claim 4, wherein the drug is a liquid suspension, a liquid dispersion, a powder, a liposome, an aqueous solution or a combination thereof.

9. The device of claim 1, wherein the propellant is a pressurized liquid.

10. The device of claim 9, wherein the pressurized liquid is hydrofluoroalkane.

11. The device of claim 10, wherein upon actuation of the device, the hydrofluoroalkane is released from the canister and comes into communication with the porous frit, whereby the hydrofluoroalkane is converted to gaseous hydrofluoroalkane.

12. The device of claim 11, wherein a minority of the pressurized liquid hydrofluoroalkane is converted to gaseous hydrofluoroalkane.

13. The device of claim 10, wherein a majority of the pressurized liquid hydrofluoroalkane is converted to gaseous hydrofluoroalkane.

14. The device of claim 1, wherein at least 64.2% of the compound is delivered to the olfactory region.

15. The device of claim 1, wherein the canister is a syringe, a syrette, or a barrel.

16. The device of claim 1, wherein the compound is not an imaging agent.

17. The device of claim 1, wherein the compound is not fluorodeoxyglucose.

18. The device of claim 1, further comprising an aiming-guide.

19. The device of claim 18, wherein the aiming guide aides in positioning the nozzle with a user's olfactory region.

20. The device of claim 18, wherein the aiming guide is an indicator which indicates the depth of insertion of the device into the user's nasal cavity.

21. The device of claim 1, further comprising an insertion port in communication with the compound chamber, the insertion port being configured to receive insertion of a compound from outside the device into the compound chamber.

22. The device of claim 21, wherein the insertion port is constructed from silicone or plastic.

23. The device of claim 1, wherein the porous frit is heterogeneously porous or homogenously porous.

24. The device of claim 1, wherein the canister is a metered dose inhaler (MDI).

25. The device of claim 1, wherein the porous frit comprises porous stainless steel having a pore size of approximately 1 to 100 microns.

26. A device for delivering a compound to an olfactory region of a nasal cavity comprising:
   a canister capable of containing a propellant,
   a diffuser in communication with the canister,
   a compound chamber in communication with the diffuser, the compound chamber capable of containing the compound, wherein the diffuser is extended into the compound in the compound chamber, and
   a nozzle in communication with the compound chamber, wherein the device is capable of delivering the compound to the olfactory region of the nasal cavity.

27. A device for delivering a compound to an olfactory region of a nasal cavity, the device comprising:
   a housing body;
   a canister configured to contain a propellant,
   a diffuser in communication with the canister,
   a compound chamber in communication with the diffuser and connected to the housing body by flanges such that there is an area between the compound chamber and the housing body, the compound chamber configured to contain the compound, and
   a nozzle in communication with the compound chamber and with the area between the compound chamber and the housing body, wherein the propellant travels both through the compound chamber and through the area between the compound chamber and the housing body.

28. A method for intranasal delivery of a compound across the blood brain comprising:
   inserting at least a portion of a device into a nasal cavity of a subject, the device including a canister containing a propellant, a compound chamber containing the compound, and a nozzle in communication with the compound chamber; and
   actuating the device thereby causing delivery of the compound to the nasal cavity, wherein compound is delivered to a brain of the subject with a direct transport percentage of at least 50%.

29. The method of claim 28, wherein the compound is suitable for the treatment of an infectious disease, oncology, or immunological disease.

30. The method of claim 28, wherein the compound is an oxime.

31. The method of claim 28, wherein the direct transport percentage is at least 60%.

32. The method of claim 31, wherein the direct transport percentage is at least 80%.

33. The method of claim 28, wherein delivery of the compound to the nasal cavity comprises deposition of at least 50% of the compound to an olfactory region of the nasal cavity.

34. The method of claim 33, wherein delivery of the compound to the nasal cavity comprises deposition of at least 60% of the compound to an olfactory region of the nasal cavity.

35. The method of claim 34, wherein delivery of the compound to the nasal cavity comprises deposition of at least 70% of the compound to an olfactory region of the nasal cavity.

36. The method of claim 28, wherein the subject is a human.

37. A method for delivering an oxime across the blood-brain barrier to a subject in need thereof comprising:
   delivering a therapeutically effective amount of an oxime intranasally to an olfactory region of a nasal cavity of the subject, wherein a concentration of the oxime in a brain of the subject five minutes following administration is higher for intranasal delivery than for intravenous injection of an equal weight of the oxime.

38. The method of claim 37, wherein the therapeutically effective amount of the oxime administered to the subject is about 0.001 mg/kg to about 100 mg/kg.

39. The method of claim 38, wherein the therapeutically effective amount of the oxime administered to the subject is about 0.01 mg/kg to about 10 mg/kg.

40. The method of claim 37, wherein delivery of the oxime provides treatment, prevention, or palliative care of an organophosphate exposure.

41. The method of claim 37, wherein the oxime is at least one of 2-pyridine aldoxime methyl chloride, 1,1-methylenebis[4-[(hydroxyimino)methyl]-pyridinium] dimethanesulfonate, 1-[[[4-(Aminocarbonyl)pyridinio]methoxy]methyl]-2-[(hydroxyimino)methyl]-pyridinium chloride, trimedoxime, or Hlo7.

42. The method of claim 41, wherein the oxime is 2-pyridine aldoxime methyl chloride.

43. The method of claim 37, wherein the oxime is a nasal dosage form.

44. The method of claim 43, wherein the nasal dosage form of the oxime is a powder, an aqueous solution, a suspension, a lipid containing product or combinations thereof.

45. The method of claim 37, wherein the subject has been exposed to an organophosphate.

46. The method of claim 45, wherein the organophosphate comprises sarin, tabun, soman, VX, diisopropylfluorophosphate or combinations thereof.

47. The method of claim 37, wherein a majority of the oxime is delivered to the olfactory region of the nasal cavity.

48. The method of claim 37, further comprising administering to the subject a nasal dosage form of a muscarinic receptor agonist or a muscarinic receptor antagonist.

49. The method of claim 37, further comprising administering to the subject a nasal dosage form of a muscarine antagonist.

50. The method of claim 49, wherein the muscarine antagonist is atropine, scopolamine or combinations thereof.

51. The method of claim 37, further comprising administering to the subject a nasal dosage form of a benzodiazepine antagonist.

52. The method of claim 51, wherein the benzodiazepine antagonist is diazepam, midazolam, lorazepam or combinations thereof.

53. The method of claim 37, further comprising administering to the subject a nasal dosage form of a benzodiazepine antagonist, a muscarinic receptor agonist, a muscarinic receptor antagonist or combinations thereof.

54. The method of claim 53, wherein the nasal dosage form is diazepam, midazolam, lorazepam, atropine, scopolamine or combinations thereof.

55. The method of claim 37, wherein the oxime is delivered to the nasal cavity of the subject before an exposure to an organophosphate.

56. The method of claim 37, wherein the oxime is delivered to the nasal cavity of the subject after an exposure to an organophosphate.

57. The method of claim 37, wherein the oxime is delivered to the nasal cavity of the subject during an exposure to an organophosphate.

58. The method of claim 37, wherein at least 53% direct transport of the oxime is to the brain.

59. The method of claim 37, wherein the oxime is propelled by a propellant to the olfactory region.

60. A device for delivering a compound to an olfactory region of a nasal cavity, the device comprising:
   a canister capable of containing a propellant,
   a diffuser in communication with the canister, the diffuser configured to convert the propellant from a liquid to a gas,
   a compound chamber in communication with the diffuser, the compound chamber configured to hold the compound, and
   a nozzle in communication with the compound chamber, wherein the device is configured to deliver the compound to the olfactory region of the nasal cavity.

61. A device for delivering a compound to an olfactory region of a nasal cavity, the device comprising:
   a canister capable of containing a propellant,
   a diffuser in communication with the canister, the diffuser being a one way check valve,
   a compound chamber in communication with the diffuser, the compound chamber capable of containing the compound, and
   a nozzle in communication with the compound chamber, wherein the device is capable of delivering the compound to the olfactory region of the nasal cavity.

* * * * *

UNITED STATES PATENT AND TRADEMARK OFFICE
CERTIFICATE OF CORRECTION

PATENT NO. : 9,550,036 B2
APPLICATION NO. : 14/017048
DATED : January 24, 2017
INVENTOR(S) : John D. Hoekman et al.

It is certified that error appears in the above-identified patent and that said Letters Patent is hereby corrected as shown below:

In the Claims

Column 29, Line 5, Claim 28, delete "the blood brain comprising:" and insert --the blood-brain barrier comprising:--

Signed and Sealed this
Thirty-first Day of December, 2019

Andrei Iancu
*Director of the United States Patent and Trademark Office*